(12) United States Patent
Kaplan et al.

(10) Patent No.: US 10,314,938 B2
(45) Date of Patent: *Jun. 11, 2019

(54) CONCENTRATED AQUEOUS SILK FIBROIN SOLUTION AND USE THEREOF

(71) Applicant: Trustees of Tufts College, Medford, MA (US)

(72) Inventors: David L. Kaplan, Concord, MA (US); Ung-Jin Kim, Daejeon (KR); Jaehyung Park, Decatur, GA (US); Hyoung-Joon Jin, Seoul (KR)

(73) Assignee: TRUSTEES OF TUFTS COLLEGE, Ballou Hall, MA (US)

( * ) Notice: Subject to any disclaimer, the term of this patent is extended or adjusted under 35 U.S.C. 154(b) by 21 days.

This patent is subject to a terminal disclaimer.

(21) Appl. No.: 15/434,484

(22) Filed: Feb. 16, 2017

(65) Prior Publication Data

US 2017/0296696 A1    Oct. 19, 2017

Related U.S. Application Data

(60) Division of application No. 14/293,308, filed on Jun. 2, 2014, now Pat. No. 9,623,147, which is a continuation of application No. 13/827,304, filed on Mar. 14, 2013, now Pat. No. 8,742,069, which is a continuation of application No. 12/425,541, filed on Apr. 17, 2009, now Pat. No. 9,084,840, which is a continuation of application No. 11/247,358, filed on Oct. 11, 2005, now Pat. No. 7,635,755, which is a continuation of application No. PCT/US2004/011199, filed on Apr. 12, 2004.

(60) Provisional application No. 60/551,186, filed on Mar. 8, 2004, provisional application No. 60/461,716, filed on Apr. 10, 2003.

(51) Int. Cl.

| | |
|---|---|
| *B29D 7/01* | (2006.01) |
| *B29L 7/00* | (2006.01) |
| *B29L 9/00* | (2006.01) |
| *C08J 3/07* | (2006.01) |
| *C08J 5/18* | (2006.01) |
| *C08J 9/00* | (2006.01) |
| *C08J 9/26* | (2006.01) |
| *C08J 9/28* | (2006.01) |
| *D01D 5/00* | (2006.01) |
| *D01F 4/02* | (2006.01) |
| *A61L 27/22* | (2006.01) |
| *A61L 27/36* | (2006.01) |
| *A61L 27/38* | (2006.01) |
| *A61L 27/52* | (2006.01) |
| *A61L 27/56* | (2006.01) |
| *B29C 39/00* | (2006.01) |
| *B29C 39/20* | (2006.01) |
| *B29C 55/00* | (2006.01) |
| *C08J 3/075* | (2006.01) |
| *C08L 89/00* | (2006.01) |
| *C07K 14/435* | (2006.01) |

(52) U.S. Cl.
CPC ......... *A61L 27/227* (2013.01); *A61L 27/3604* (2013.01); *A61L 27/38* (2013.01); *A61L 27/52* (2013.01); *A61L 27/56* (2013.01); *B29C 39/003* (2013.01); *B29C 39/203* (2013.01); *B29C 55/005* (2013.01); *B29D 7/01* (2013.01); *C07K 14/43536* (2013.01); *C07K 14/43586* (2013.01); *C08J 3/07* (2013.01); *C08J 3/075* (2013.01); *C08J 5/18* (2013.01); *C08J 9/0061* (2013.01); *C08J 9/26* (2013.01); *C08J 9/28* (2013.01); *C08L 89/00* (2013.01); *D01D 5/0007* (2013.01); *D01F 4/02* (2013.01); *A61L 2430/02* (2013.01); *B29K 2089/00* (2013.01); *B29L 2007/00* (2013.01); *B29L 2009/00* (2013.01); *C08J 2201/0444* (2013.01); *C08J 2201/0504* (2013.01); *C08J 2205/022* (2013.01); *C08J 2389/00* (2013.01); *Y10T 428/249921* (2015.04); *Y10T 442/10* (2015.04); *Y10T 442/60* (2015.04)

(58) Field of Classification Search
None
See application file for complete search history.

(56) References Cited

U.S. PATENT DOCUMENTS

| | | | |
|---|---|---|---|
| 1,989,005 | A | 1/1935 | Fink et al. |
| 4,233,212 | A | 11/1980 | Otoi et al. |
| 4,806,355 | A | 2/1989 | Goosen et al. |

(Continued)

FOREIGN PATENT DOCUMENTS

| | | |
|---|---|---|
| CA | 2405850 A1 | 10/2002 |
| CN | 1483866 A | 3/2004 |

(Continued)

OTHER PUBLICATIONS

Ajisawa, A., Dissolution of silk fibroin with calciumchloride/ethanol aqueous solution, J. Seric. Sci. Jpn. 67(2):91-94 (1998).
Altman, G. H. et al., Silk-based biomaterials, Biomaterials, 24:401-416 (2003).
Altman, G.H. et al., Silk matrix for tissue engineered anterior cruciate ligaments, Biomaterials 23:4131-41 (2002).
Asakura, T. and Kaplan, D. Silk Production and Processing, Encyclopedia of Agricultural Science, 4:1-11 (1994).

(Continued)

*Primary Examiner* — Anand U Desai
(74) *Attorney, Agent, or Firm* — Quarles & Brady LLP

(57) ABSTRACT

The present invention provides for concentrated aqueous silk fibroin solutions and an all-aqueous mode for preparation of concentrated aqueous fibroin solutions that avoids the use of organic solvents, direct additives, or harsh chemicals. The invention further provides for the use of these solutions in production of materials, e.g., fibers, films, foams, meshes, scaffolds and hydrogels.

18 Claims, 12 Drawing Sheets

Specification includes a Sequence Listing.

(56) References Cited

U.S. PATENT DOCUMENTS

| | | | |
|---|---|---|---|
| 4,820,418 | A | 4/1989 | Hirotsu et al. |
| 5,015,476 | A | 5/1991 | Cochrum et al. |
| 5,047,507 | A | 9/1991 | Buchegger et al. |
| 5,093,489 | A | 3/1992 | Diamantoglou |
| 5,245,012 | A | 9/1993 | Lombari et al. |
| 5,263,992 | A | 11/1993 | Guire |
| 5,270,419 | A | 12/1993 | Domb |
| 5,290,494 | A | 3/1994 | Coombes et al. |
| 5,576,881 | A | 11/1996 | Doerr et al. |
| 5,606,019 | A | 2/1997 | Cappello |
| 5,728,810 | A | 3/1998 | Lewis et al. |
| 5,770,193 | A | 6/1998 | Vacanti et al. |
| 5,902,800 | A | 5/1999 | Green et al. |
| 5,994,099 | A | 11/1999 | Lewis et al. |
| 6,110,590 | A | 8/2000 | Zarkoob et al. |
| 6,123,819 | A | 9/2000 | Peeters |
| 6,127,143 | A | 10/2000 | Gunasekaran |
| 6,175,053 | B1 | 1/2001 | Tsubouchi |
| 6,245,537 | B1 | 6/2001 | Williams et al. |
| 6,267,776 | B1 | 7/2001 | O'Connell |
| 6,302,848 | B1 | 10/2001 | Larson et al. |
| 6,310,188 | B1 | 10/2001 | Mukherjee |
| 6,325,810 | B1 | 12/2001 | Hamilton et al. |
| 6,337,198 | B1 | 1/2002 | Levene et al. |
| 6,372,244 | B1 | 4/2002 | Antanavich et al. |
| 6,379,690 | B2 | 4/2002 | Blanchard et al. |
| 6,387,413 | B1 | 5/2002 | Miyata et al. |
| 6,395,734 | B1 | 5/2002 | Tang et al. |
| 6,423,252 | B1 | 7/2002 | Chun et al. |
| 6,592,623 | B1 | 7/2003 | Bowlin et al. |
| 6,815,427 | B2 | 11/2004 | Tsubouchi et al. |
| 6,902,932 | B2 | 6/2005 | Altman et al. |
| 7,041,797 | B2 | 5/2006 | Vollrath |
| 7,057,023 | B2 | 6/2006 | Islam et al. |
| 7,285,637 | B2 | 10/2007 | Armato et al. |
| 7,635,755 | B2 | 12/2009 | Kaplan et al. |
| 7,662,409 | B2 | 2/2010 | Masters |
| 7,674,882 | B2 | 3/2010 | Kaplan et al. |
| 7,727,575 | B2 | 6/2010 | Kaplan et al. |
| 7,842,780 | B2 | 11/2010 | Kaplan et al. |
| 7,960,509 | B2 | 6/2011 | Kaplan et al. |
| 8,071,722 | B2 | 12/2011 | Kaplan et al. |
| 8,361,617 | B2 * | 1/2013 | Kaplan ............ A61L 27/227 428/357 |
| 8,614,293 | B2 | 12/2013 | Kaplan et al. |
| 8,742,069 | B2 | 6/2014 | Kaplan et al. |
| 9,084,840 | B2 | 7/2015 | Kaplan et al. |
| 2002/0028243 | A1 | 3/2002 | Masters |
| 2003/0007991 | A1 | 1/2003 | Masters |
| 2003/0183978 | A1 | 10/2003 | Asakura |
| 2004/0005363 | A1 | 1/2004 | Tsukada et al. |
| 2004/0266992 | A1 | 12/2004 | Migliaresi et al. |
| 2007/0187862 | A1 | 8/2007 | Kaplan et al. |
| 2007/0212730 | A1 | 9/2007 | Vepari et al. |
| 2008/0085272 | A1 | 4/2008 | Kaplan et al. |
| 2008/0293919 | A1 | 11/2008 | Kaplan et al. |
| 2009/0202614 | A1 | 8/2009 | Kaplan et al. |
| 2009/0232963 | A1 | 9/2009 | Kaplan et al. |
| 2009/0234026 | A1 | 9/2009 | Kaplan et al. |
| 2010/0028451 | A1 | 2/2010 | Kaplan et al. |
| 2010/0046902 | A1 | 2/2010 | Kaplan et al. |
| 2010/0055438 | A1 | 3/2010 | Kaplan et al. |
| 2010/0063404 | A1 | 3/2010 | Kaplan et al. |
| 2010/0065784 | A1 | 3/2010 | Kaplan et al. |
| 2010/0068740 | A1 | 3/2010 | Kaplan et al. |
| 2010/0070068 | A1 | 3/2010 | Kaplan et al. |
| 2010/0096763 | A1 | 4/2010 | Kaplan et al. |
| 2010/0120116 | A1 | 5/2010 | Kaplan et al. |
| 2010/0178304 | A1 | 7/2010 | Wang et al. |
| 2010/0191328 | A1 | 7/2010 | Kaplan et al. |
| 2010/0196447 | A1 | 8/2010 | Kaplan et al. |
| 2011/0046686 | A1 | 2/2011 | Kaplan et al. |
| 2011/0076384 | A1 | 3/2011 | Cannizzaro et al. |
| 2011/0135697 | A1 | 6/2011 | Omenetto et al. |
| 2011/0152214 | A1 | 6/2011 | Boison et al. |
| 2011/0171239 | A1 | 7/2011 | Kaplan et al. |
| 2012/0121820 | A1 | 5/2012 | Kaplan et al. |
| 2012/0123519 | A1 | 5/2012 | Lovett et al. |
| 2012/0171770 | A1 | 7/2012 | Numata et al. |
| 2013/0165004 | A1 | 6/2013 | Kaplan et al. |
| 2013/0190222 | A1 | 7/2013 | Kaplan et al. |
| 2015/0038043 | A1 | 2/2015 | Kaplan et al. |

FOREIGN PATENT DOCUMENTS

| | | |
|---|---|---|
| EP | 1440088 A2 | 7/2004 |
| GB | 1182153 A | 2/1970 |
| JP | S58-38449 B2 | 8/1983 |
| JP | 60-142259 A | 7/1985 |
| JP | 60-259677 | 12/1985 |
| JP | H01-118544 A | 5/1989 |
| JP | H05-43600 A | 2/1993 |
| JP | H06-346314 | 12/1994 |
| JP | 08-295697 | 11/1996 |
| JP | 10-36676 | 2/1998 |
| JP | 2000-273264 A | 10/2000 |
| JP | 2003-192807 A | 7/2003 |
| JP | 2004-068161 A | 3/2004 |
| WO | WO-1997/008315 A1 | 3/1997 |
| WO | WO-1999/001089 A1 | 1/1999 |
| WO | WO-2001/036531 | 5/2001 |
| WO | WO-01/056626 A1 | 8/2001 |
| WO | WO-2002/072931 | 9/2002 |
| WO | WO-03/022909 A1 | 3/2003 |
| WO | WO-03/038033 A2 | 5/2003 |
| WO | WO-2003/060207 A1 | 7/2003 |
| WO | WO-04/000915 A2 | 12/2003 |
| WO | WO-04/041845 A2 | 5/2004 |
| WO | WO-2005/012606 A2 | 2/2005 |
| WO | WO-05/123114 A2 | 12/2005 |
| WO | WO-2008/127405 A2 | 10/2008 |
| WO | WO-2011/006133 A2 | 1/2011 |

OTHER PUBLICATIONS

Asakura, T. et al., Conformational characterization of Bombyx mori silk fibroin in the solid state by high-frequency carbon-13 cross polarization-magic angle spinning NMR, x-ray diffraction, and infrared spectroscopy, Macromolecules, 18(10):1841-1845 (1985).

Asakura, T. et al., NMR of silk fibroin 2. 13C NMR study of the chain dynamics and solution structure of Bombyx mori silk fibroin, Macromolecules, 17:1075-1081 (1984).

Author Not Known, Dulbecco's Modified Eagle's Medium—DME, DMEM, Sigma Aldrich, 4 pages, retrieved from the internet on Mar. 15, 2016, www.sigmaaldrich.com/life-science/cell-culture/classical-media-salts/dmem.html.

Ayub, Z. H. et al., Mechanism of the Gelation of Fibroin Solution, Viosci. Biotech. Biochem, 57(11):1910-1912 (1993).

Bini, E. et al., Mapping domain structures in silks from insects and spiders related to protein assembly, Journal of Molecular Biology, 335(1):27-40 (2004).

Braun, F. N. and Viney, C., Modelling self assembly of natural silk solutions, Int. J. Bio. Macromol., 32:59-65 (2003).

Caplan, A. I., The Messengenic Process, Clinics in Plastic Surgery, 21(3):429-435 (1994).

Cappello et al., In situ self-assembling protein polymer gel systems for administration, delivery, and release of drugs, J. Control Release, 53:105-117 (1998).

Chen et al., pH sensitivity and ion sensitivity of hydrogels based on complex-forming chitosan/silk fibroin interpenetrating polymer network, J. Appl. Polymer Sci., 65:2257-62 (1997).

Chen et al., Separation of alcohol-water mixture by pervaporation through a novel natural polymer blend membrane-chitosan/silk fibroin blend membrane, J. Appl. Polymer Sci., 73:975-980 (1999).

Chen, J. and Minoura, N., Transport of pharmaceuticals through silk fibroin membrane, Polymer, 35(13):2853 (1994).

Chen, X. et al., Conformation Transition Kinetics of Bombyx mori Silk Protein, Proteins: Structure, Function, and Bioinformatics, 68:223-231 (2007).

(56) References Cited

OTHER PUBLICATIONS

Common Organic Solvents: Table of Properties1, Division of Organic Chemistry American Chemical Society, retrieved from internet on Oct. 5, 2016, www.organicdivision.org/orig/organic_solvents.html, 2 pages.
Curtis, R.A. et al., Hydrophobic forces between protein molecules in aqueous solutions of concentrated electrolyte, Biophysical Chemistry, 98:249-265 (2002).
Database WPI Week 198205, Derwent Publications Ltd., London, GB; AN 1982-09092E & JP 56 166235 A, Abstract (Dec. 21, 1981).
Demura, M. and Asakura, T., Porous membrane of Bombyx mori silk fibroin: structure characterization, physical properties and application to glucose oxidase immobilization, J. Membrane Science, 59:39-52 (1991).
Demura, M. et al., Immobilization of Biocatalysts with Bombyx mori Silk Fibroin by Several Kinds of Physical Treatment and Its Application to Glucose Sensors, Biosensors, 4(6):361-372 (1989).
Derwent Record, Abstract of JP 08295697 A2, Production of Aqueous Solution of Silk Fibroin at High Concentration (Nov. 12, 1996).
Deuel, T. F. and Zhang, N., Growth Factors, Principles of Tissue Engineering, Second Edition, Chapter 12, pp. 129-141 (2000).
Dinerman, A. A. et al., Solute Diffusion in genetically engineered silk-elastinlike protein polymer hydrogels, J. Control. Release, 82:277-287 (2002).
Doshi et al., Electrospinning Process and Applications of Electrospun Fibers, J/Electrostatics, 35: 151-160 (1995).
Fedarko, N. S. et al., Temporal Regulation of Hyaluronan and Proteoglycan Metabolism by Human Bone Cells in Vitro, J. Bio. Chem., 265(21):12200-12209 (1990).
Ferguson, C. et al., Does Adult fracture repair recapitulate embryonic skeletal formation?, Mech. Dev., 87:57-66 (1999).
Fisher, L. W. et al., Proteoglycans of Developing Bone, J. Bio. Chem., 258(10):6588-6594 (1983).
Foo, C. W. P. and Kaplan, D. L., Genetic engineering of fibrous proteins: spider dragline silk and collagen, Adv. Drug Deliver. Rev., 54:1131-1143 (2002).
Foreign Counterpart Application EP 03761306: Supplementary European Search Report (dated Sep. 14, 2010).
Freddi et al., Silk fibroin/cellulose blend films: preparation, structure, and physical properties, J Appl Polymer Sci, 56:1537-1545 (1995).
Freshney, R. I, Maintenance of Primary and Early Passage Cultures, Methods of Tissue Engineering, Chapter 3, pp. 37-53 (2002).
Freshney, R.I., Culture of Animal Cells, a Manual of Basic Technique, Hoboken NJ, (2000).
Friedenstein et al., Bone marrow osteogenic stem cells: in vitro cultivation and transplantation in diffusion chambers, Cell Tissue Kinet, 20:263-272 (1987).
Friedenstein, A. J., Precursor Cells of Mechanocytes, International Review of Cytology, 47:327-359 (1976).
Gerber, H. et al., VEGF couples hypertrophic cartilage remodeling, ossification and angiogenesis during enochondral bone formation, Nat. Med., 5:623-628 (1999).
Grigsby, J.J. et al., Cloud-point temperatures for lysozyme in electrolyte solutions: effect of salt type, salt concentration and pH, Biophys. Chem., 91:231-243 (2001).
Ha, S.W. et al., Structural Studies of Bombyx mori Silk Fibroin during Regeneration from Solutions and Wet Fiber Spinning, Biomacromolecules, 6:1722-1731 (2005).
Hanawa et al., New Oral Dosage Form for Elderly Patients: Preparation and Characterization of Silk Fibroin Gel., Chem. Pham. Bull., 43(2):284-288 (1995).
Harris, L. D. Et al., Open pore biodegradable matrices formed with gas foaming, Journal of Biomedical Material Research, 42(3):396-402 (1998).
Hersel, U. et al., RGD modified polymers: biomaterials for stimulated cell adhesion and beyond, Biomaterials, 24:4385-415 (2003).
Herzog, E. L. et al., Plasticity of marrow-derived stem cells, Blood, 102:3483-3493 (2003).

Hijirida et al., 13C NMR of Nephila clavipes Marjo Ampullate Silk Gland, Biophysical Journal 71:3442-3447 (1996).
Hinman, M.B. et al., Synthetic spider silk: a modular fiber, Trends Biotechnol, 18(9):374-9 (2000).
Holy, et al., Use of a biomimetic strategy to engineer bone, J Biomed Mater Res, 65A:447-453 (2003).
Hu et al., Regulation of Silk Material Structure by Temperature-Controlled Water Vapor Annealing, Biomacraomolecules, 12:1686-1696 (2011).
Huang et al., Engineered collagen-PEO nanofibers and fabrics, J Biomater Sci Polymer Edn, 12(9):979-993 (2001).
Huang et al., Generation of Synthetic Elastin-Mimetic Small Diameter Fibers and Fiber Networks, Macromolecules, 33:2989-2997 (2000).
International Search Report for PCT/US2004/011199, 1 page (dated Sep. 8, 2005).
Jin, H.J. and Kaplan, D.L., Mechanism of silk processing in insects and spiders, Nature 424(6952):1057-1061 (2003).
Jin, H.J. et al., Electrospinning Bombyx mori silk with poly(ethylene oxide), Biomacromolecules, 3(6):1233-9 (2002).
Jin, H.J. et al., Water-Stable Silk Films with Reduced β-Sheet Content, Advanced Functional Materials, 15:1241-1247 (2005).
Kang, G. et al., Effects of poloxamer on the gelation of silk fibroin, Macromol. Rapid Commun., 21:788-791 (2000).
Katoh, K. et al., Novel approach to fabricate keratin sponge scaffolds with controlled pore size and porosity, Biomaterials, 25:4255-4262 (2004).
Kim, U.J. et al., Structure and properties of silk hydrogels, Biomacromolecules, 5(3):786-92 (2004).
Kweon et al., Preparation of Semi-Interpreting Polymer Networks Composed of Silk Fibroin and Poly( ethylene glycol) Macromer, J. Appl. Polymer Sci., 80:1848-1853 (2001).
Lazaris, A. et al., Spider silk fibers spun from soluble recombinant silk produced in mammalian cells, Science, 295 (5554):472-6 (2002); Supplementary Material, retrieved from internet on Aug. 5, 2015, www.sciencemag.org/content/295/5554/472/suppl/DC1, 3 pages.
Lazaris, A. et al., Spider silk fibers spun from soluble recombinant silk produced in mammalian cells, Science. 295(5554):472-6 (2002).
Lee, K.Y. et al., Hydrogels for Tissue Engineering, Chemical Review 101(8):1869-1879 (2001).
Li, et al., Study on Porous Silk Fibroin Materials. I. Fine Structure of Freeze Dried Silk Fibroin, J Appl Polym Sci, 79:2185-2191 (2001).
Li, G.Y. et al., The natural silk spinning process—A nucleation-dependent aggregation mechanism?, Eur. J. Biochem., 268:6600-6606 (2001).
Li, M. et al., Study on Porous Silk Fibroin Materials. II. Preparation and Characteristics of Spongy Porous Silk Fibroin Materials, Journal of Applied Polymer Science, 79:2192-2199 (2001).
Liang, C. X., et al., Improvements of the physical properties of fibroin membranes with sodium alginate, J. Appl. Polymer Sci., 1937-1943 (1992).
Lu, Q. et al., Water-insoluble silk films with silk I structure, Acta Biomaterialia, 6(4):1380-1387 (2010).
Lucas, F. et al., The Silk Fibroin, Advanced Protein Chemicals, 13:107-242 (1958).
Ma, L. et al., Collagen/chitosan porous scaffolds with improved biostability for skin tissue engineering, Biomaterials, 24:4833-4841 (2003).
Mackay, A. M. et al., Chondrogenic Differentiation of Cultured Human Mesenchymal Stem Cells from Marrow, Tissue Eng., 4(4):415-428 (1998).
Magoshi J. et al., Biospinning (Silk Fiber Formation, Multiple Spinning Mechanisms), Polymerics Materials Encyclopedia, vol. 1, A-B, 667-679 (1996).
Maquet, V. et al., Porous poly(a-hydroxyacid)/Bioglass composite scaffolds for bone tissue engineering. I: preparation and in vitro charachterisation, Biomaterials, 25:4185-4194 (2004).
Megeed et al., Controlled Release of Plasmid DNA from a Genetically Engineered Silk-Elastin like Hydrogel, Pharmaceutical Research, 19(7):954-959 (2002).

(56) References Cited

OTHER PUBLICATIONS

Megeed, Z. et al., Genetically engineered silk-elastinlike protein polymers for controlled drug delivery, Adv. Drug Delivery Rev., 54:1075-1091 (2002).

Meinel et al., Bone Tissue Engineering Using Human Mesenchymal Stem Cells: Effects of Scaffold Material and Medium Flow, Ann Biomed Eng., 32(1):112-22 (2004).

Min, B.M. et al., Regenerated Silk Fibroin Nanofibers: Water Vapor-Induced Structural Changes and Their Effects on the Behavior of Normal Human Cells, Macromol. Biosci., 6(4):285-292 (2006).

Min, S. et al., Preparation and Characterization of Crosslinked Porous Silk Fibroin Gel, Sen'i Gakkaishi, 54(2):85-92 (1998).

Minoura, N. et al., Fine structure and oxygen permeability of silk fibroin membrane treated with methanol, Polymer, 31(2): 265-269 (1990).

Mita, K. et al., Highly Repetitive Structure and Its Organization of the Silk Fibroin Gene, J. Mol. Evol., 38:583-592 (1994).

Nakawaga, T. et al., Characterization of the development of ectopic chondroid/bone matrix and chondrogenic/osteogenic cells during osteoinduction by rhBMP-2: a histochemical and ultrastructural study, Oral Diseases, 9:255-263 (2003).

Nazarov, R. et al., Porous 3-D scaffolds from regenerated silk fibroin, Biomacromolecules, 5(3):718-726 (2004).

Ochi, A. et al., Rheology and dynamic light scattering of silk fibroin solution extracted from the middle division of Bombyx mori silkworm, Biomacromolecules, 3:1187-1196 (2002).

Panilaitis, B. et al., Macrophage responses to silk, Biomaterials, 24:3079-3085 (2003).

Parsegian, V.A. et al., Osmotic Stress for the Direct Measurement of Intermolecular Forces, Methods of Enzymology, 127:400-416 (1986).

Petrini et al., Silk fibroin-polyurethane scaffolds for tissue engineering, Journal of Materials Science: Materials in Medicine, 12:849-853 (2001).

Radisic, M. et al., High-Density Seeding of Myocyte Cells for Cardiac Tissue Engineering, Biotechnology and Bioengineering, 82(4):403-414 (2003).

Reneker D.H. and Chun, I., Nanometre diameter fibres of polymer, produced by electrospinning, Nanotechnology, 7:216-223 (1996).

Robinson, D.R. et al., The Effect of Concentrated Salt Solutions on the Activity Coefficient of Acetyltetraglycine Ethyl Ester, J. Am. Chem. Soc., 87(11):2470-2479 (1965).

Sato, G. H and Barnes, D. W., Animal Cell Culture, Principles of Tissue Engineering, Second Edition, Chapter 10, pp. 111-118 (2000).

Sawyer et al., Dextran therapy in thrombophlebitis. Abstract, JAMA, 191(9):740-742 (1965).

Schaffner P. and Dard, M.M., Structure and function of RGD peptides involved in bone biology, Cell Mol Life Sci., 60:119-32 (2003).

Scheibel, T., Spider silks: recombinant synthesis, assembly, spinning, and engineering of synthetic proteins, Microb. Cell Fact., 3(1):14 (2004).

Sikavitsas, V.I. et al., Formation of three-dimensional cell/polymer constructs for bone tissue engineering in a spinner flask and a rotating wall vessel bioreactor, J. Biomed. Mater. Res., 62:136-148 (2002).

Singh, K. et al., Physiological Properties and Differential Glycosylation of Phosphorylated and Nonphosphorylated Forms of Osteopontin Secreted by Normal Rat Kidney Cells, Journal of Biological Chemistry, 265(30):18696-18701 (1990).

Sofia et al. Functionalized Silk-Based Biomaterials for Bone Formation, J. Biomed. Mater. Res. 54:139-148 (2001).

Supplementary European Search Report for EP 04785887.3, 3 pages (dated Jul. 16, 2007).

Thomson, R. C. et al., Hydroxyapatite fiber reinforced poly(alpha-hydroxy ester) foams for bone regeneration, Biomaterials, 19:1935-1943 (1998).

Thomson, R. C. et al., Polymer Scaffold Processing, Principles of Tissue Engineering, Second Edition, Chapter 21, 251-262 (2000).

Tsukada, M. et al., Structural Changes of Silk Fibroin Membranes Induced by Immersion in Methanol Aqueous Solutions, Journal of Polym. Sci. Part B Polym. Physics, 32:961-968 (1994).

Valluzzi, R. et al., Methionine Redox Controlled Crystallization of Biosynthetic Silk Spidroin, J. Phys. Chem., 103(51):11382-11392 (1999).

Vollrath, F. et al., Silk production in a spider involves acid bath treatment, The Royal Society, 265:817-820 (1998).

Vunjak-Novakovic et al., Dynamic Cell Seeding of Polymer Scaffolds for Cartilage Tissue Engineering, Biotechnology Progress, 14(2):193-202 (1998).

Wang, X. et al., Biomaterial Coatings by Stepwise Deposition of Silk Fibroin, Langmuir, 21(24): 11335-11341 (2005).

Written Opinion for PCT/US2004/011199, 3 pages (dated Sep. 8, 2005).

Yamada et al., AFM observation of silk fibroin on mica substrates: morphologies reflecting the secondary structure, Thin Solid Films, 440:208-16 (2003).

Yao, K. L. et al., Temporal Changes in Matrix Protein Synthesis and mRNA Expression During Mineralized Tissue Formation by Adult Rat Bone Marrow Cells in Culture, Journal of Bone and Mineral Research, 9:231-2140 (1994).

Zhang, R.Y., et al., Poly(alpha-hydroxyl acids)/hydroxyapatite porous composites for bone-tissue engineering. I. Preparation and morphology, J. Biomed. Mater. Res., 44:446-455 (1999).

Zhou et al., Preparation of a novel core-shell nanostructured gold colloid-silk fibroin bioconjugate by the protein in situ redox technique at room temperature, Chem Commun, 2518-2519 (2001).

\* cited by examiner

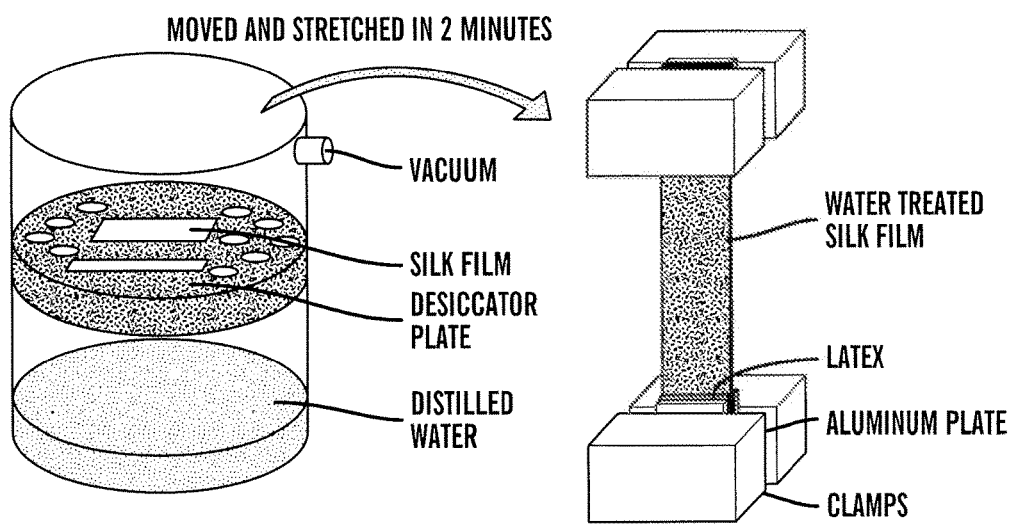
*FIG. 5A*  *FIG. 5B*

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atggggaagg tgaaggtcg                                                19

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
taaaagccct ggtgacc                                                  17

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
cgcccaatac gaccaaatcc gttgac                                        26

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ala Gly Ala Gly Ser
1               5

CONCENTRATED AQUEOUS SILK FIBROIN SOLUTION AND USE THEREOF

CROSS-REFERENCE TO RELATED APPLICATIONS

This application is a divisional of U.S. patent application Ser. No. 14/293,308, filed on Jun. 2, 2014, which is a continuation of U.S. patent application Ser. No. 13/827,304 filed on Mar. 14, 2013 and issued as U.S. Pat. No. 8,742,069 on Jun. 3, 2014, which is a continuation of U.S. patent application Ser. No. 12/425,541 filed on Apr. 17, 2009 and issued as U.S. Pat. No. 9,084,840 on Jul. 21, 2015, which is a continuation of U.S. patent application Ser. No. 11/247,358 filed on Oct. 11, 2005 and issued as U.S. Pat. No. 7,635,755 on Dec. 22, 2009, which is a continuation of International Application No. PCT/US2004/011199 filed on Apr. 12, 2004, which designated the U.S., and which claims the benefit under 35 U.S.C § 119(e) of U.S. Provisional Application No. 60/461,716 filed on Apr. 10, 2003, and U.S. Provisional Application No. 60/551,186 filed on Mar. 8, 2004, the contents of each of which are incorporated herein by reference in their entireties.

GOVERNMENT SUPPORT

This invention was supported by the NIH, the NSF and the Air Force (subcontract from Foster Miller) Grant Nos. R01EB003210, R01DE13405-01A1, DMR-0090384, F49620-01-C-0064. The government has certain rights in this invention.

SEQUENCE LISTING

The instant application contains a Sequence Listing which has been submitted in ASCII format via EFS-Web and is hereby incorporated by reference in its entirety. Said ASCII copy, created on Mar. 14, 2013, is named 700355-053849-C5_SequenceListing and is 1,367 bytes in size.

FIELD OF THE INVENTION

The present invention relates generally to methods for preparation of concentrated aqueous silk fibroin solutions and to the use of these solutions in the production of silk fibroin materials such as, fibers, films, sponge-like porous foams, 3-dimensional scaffolds, and hydrogels. In particular, an all-aqueous means for preparation of silk fibroin solutions is described.

BACKGROUND OF THE INVENTION

Silk is a well described natural fiber produced by the silkworm, *Bombyx mori*, which has been used traditionally in the form of threads in textiles for thousands of years. This silk contains a fibrous protein termed fibroin (both heavy and light chains) that form the thread core, and glue-like proteins termed sericin that surround the fibroin fibers to cement them together. The fibroin is a highly insoluble protein containing up to 90% of the amino acids glycine, alanine and serine leading to β-pleated sheet formation in the fibers (Asakura, et al., *Encylopedia of Agricultural Science*, Arntzen, C. J., Ritter, E. M. Eds.; Academic Press: New York, N.Y., 1994; Vol. 4, pp 1-11).

The unique mechanical properties of reprocessed silk such as fibroin and its biocompatibility make the silk fibers especially attractive for use in biotechnological materials and medical applications. Silk provides an important set of material options for biomaterials and tissue engineering because of the impressive mechanical properties, biocompatibility and biodegradability (Altman, G. H., et al., *Biomaterials* 2003, 24, 401-416; Cappello, J., et al., *Control. Release* 1998, 53, 105-117; Foo, C. W. P., et al., *Adv. Drug Deliver. Rev.* 2002, 54, 1131-1143; Dinerman, A. A., et al., *J Control. Release* 2002, 82, 277-287; Megeed, Z., et al., *Adv. Drug Deliver. Rev.* 2002, 54, 1075-1091; Petrini, P., et al., *J. Mater. Sci-Mater. M* 2001, 12, 849-853; Altman, G. H., et al., *Biomaterials* 2002, 23, 4131-4141; Panilaitis, B., et al., *Biomaterials* 2003, 24, 3079-3085). For example, 3-dimensional porous silk scaffolds have been described for use in tissue engineering (Meinel et al., *Ann Biomed Eng.* 2004 January; 32(1):112-22; Nazarov, R., et al., *Biomacromolecules* in press). Further, regenerated silk fibroin films have been explored as oxygen- and drug-permeable membranes, supports for enzyme immobilization, and substrates for cell culture (Minoura, N., et al., *Polymer* 1990, 31, 265-269; Chen, J., et al., Minoura, N., Tanioka, A. 1994, 35, 2853-2856; Tsukada, M., et al., *Polym. Sci. Part B Polym. Physics* 1994, 32, 961-968). In addition, silk hydrogels have found numerous applications in tissue engineering, as well as in drug delivery (Megeed et al., *Pharm Res.* 2002 July; 19(7): 954-9; Dinerman et al., *J Control Release.* 2002 Aug. 21; 82(2-3):277-87).

However, in order to prepare silk based materials described above, chemical agents or organic solvents, such as hexafluoroisopropanol (HFIP), have been used for cross-linking or for the processing (Li, M., et al., *J. Appl. Poly. Sci.* 2001, 79, 2192-2199; Min, S., et al., *Sen'i Gakkaishi* 1997, 54, 85-92; Nazarov, R., et al., *Biomacromolecules* in press). For example, HFIP is used to optimize solubility of the silk and methanol is used to induce an amorphous to β-sheet conformation transition in the fibroin, in order to generate water-stable silk structures.

The use of organic solvents in the preparation of silk fibroin materials represents a significant drawback, as organic solvents pose biocompatibility problems when the processed materials are exposed to cells in vitro or in vivo. Organic solvents can also change the properties of fibroin material. For example, the immersion of silk fibroin films in organic solvents such as methanol causes dehydration of the hydrated or swollen structure, leading to crystallization and thus, loss of solubility in water. Further, with respect to tissue engineering scaffolds, the use of organic solvents can render the silk material to be less degradable. Thus, there is a need in the art for the development of silk based materials that can be formed in the absence of chemical cross-linking and/or organic solvents.

SUMMARY OF THE INVENTION

The present invention provides for concentrated aqueous silk fibroin solutions and an all-aqueous mode for preparation of concentrated aqueous fibroin solutions that avoids the use of organic solvents or harsh chemicals. The invention further provides for the use of these solutions in production of materials, e.g., fibers, films, foams, meshes, scaffolds and hydrogels.

In one embodiment, an aqueous silk fibroin solution is provided that has a fibroin concentration of at least 10 wt % and wherein said solution is free of organic solvents. Also provided are aqueous silk fibroin solutions wherein the fibroin concentration is at least 15 wt %, at least 20 wt %, at least 25 wt %, or at least 30 wt %. If desired, the solution can be combined with a biocompatible polymer before processing.

The fibroin of the aqueous silk fibroin solution can be obtained from a solution containing a dissolved silkworm silk, e.g. from *Bombyx mori*, a dissolved spider silk, e.g. from *Nephila clavipes*, or from a solution containing a genetically engineered silk.

In one embodiment of the invention, the aqueous silk fibroin solutions described herein, further comprise a therapeutic agent. Therapeutic agents include, for example, proteins, peptides, nucleic acids and small molecule drugs.

In another embodiment, a method for the production of a concentrated aqueous fibroin solution is provided. The method comprises preparing an aqueous silk fibroin solution and dialyzing the solution against a hygroscopic polymer for a sufficient time to result in an aqueous fibroin solution of at least 10 wt %.

Hygroscopic polymers useful in the method of the present invention, include, for example, polyethylene glycol, amylase, or sericin. Preferably, the hygroscopic polymer is a polyethylene glycol (PEG) with a molecular weight of 8,000 to 10,000 g/mol. Most preferably, the PEG has a concentration of 25-50%.

In one embodiment, a method for the production of a fiber is provided. The method comprises processing the concentrated aqueous silk fibroin solution to form a fiber. Processing includes, for example electrospinning or wet spinning. Alternatively, a fiber can be pulled directly from the solution. If desired, the fiber can be treated with methanol, preferably by immersion, after processing. The fiber is then preferably washed with water.

A composition comprising a fiber that is produced by the method of the present invention and a therapeutic agent is also provided.

In another embodiment, a method of producing a silk foam is provided. The method comprises processing the concentrated aqueous silk solution of the invention to produce a foam. Processing methods include, for example, salt leaching, gas foaming, micropatterning, or by contacting solution with a salt particle. The salt is preferably monovalent, e.g. NaCl, KCl, KFl, or NaBr. Alternatively, divalent salts, e.g. $CaCl_2$, $MgSO_4$, or $MgCl_2$, may also be used.

A composition comprising a foam produced by the method of the present invention and a therapeutic agent is also provided.

In another embodiment, a method of producing a film is provided. The method casting the concentrated aqueous salt solution to form a film. In certain embodiments, it is useful to contact the film with water vapor. In addition, the film can be stretched mono-axially and bi-axially.

A composition comprising a film that is produced by the method of the present invention and a therapeutic agent is also provided.

In another embodiment, a method of producing a silk hydrogel is provided. The method comprises inducing a sol-gel transition in the concentrated aqueous silk solution of the invention.

The sol-gel transition can be induced by an increase in the silk fibroin concentration, an increase in temperature, a decrease in pH, an increase in the concentration of salt (e.g. KCl, NaCl, or $CaCl_2$.), or by addition of a polymer (e.g. polyethylene oxide (PEO).

A composition comprising a silk hydrogel that is produced by the method of the present invention and a therapeutic agent is also provided.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

FIGS. 5a and 5b illustrate one embodiment of the present invention for silk film preparation including (FIG. 5a) water treatment and (FIG. 5b) stretching.

(FIG. 8c) 37° C. Values are average±standard derivation of 7 samples.

DETAILED DESCRIPTION OF THE INVENTION

Figure 1:
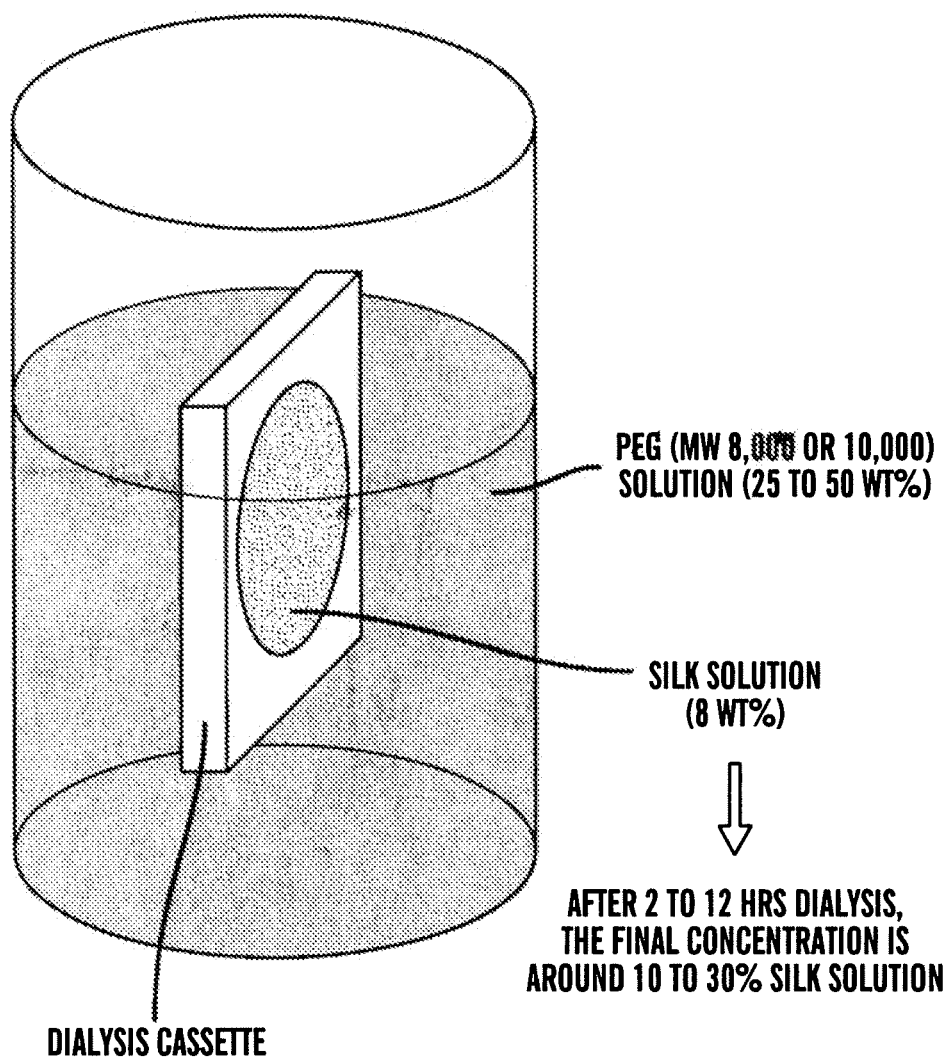
FIG. 1 illustrates one embodiment of the method of the present invention to make highly concentrated regenerated silk fibroin solution.

Methods for preparation of concentrated aqueous silk fibroin solutions in the absence of organic solvents or harsh chemicals are described. The process comprises forming a solution comprising silk fibroin. Preferably, the solution is in an aqueous salt, such as lithium bromide. The solution is then dialyzed against a hygroscopic polymer for a sufficient time to result in an aqueous silk fibroin solution of between 10-30 wt % or greater. A preferred hyproscopic polymer is polyethylene glycol (PEG).

We have discovered that increasing the viscosity of the aqueous silk fibroin solution to at least 10 wt % allows for the formation of fibers by electrospinning, for the formation of porous 3-dimensional tissue engineering scaffolds, and for other applications, e.g., formation of foams and films, while avoiding the use of organic solvents that can pose problems when the processed materials are exposed to cells in vitro or in vivo. Dialysis of the solution against a hygroscopic polymer is also sufficient to control water content in the formation of silk hydrogels.

As used herein, the term "fibroin" includes silkworm fibroin and insect or spider silk protein (Lucas et al., *Adv. Protein Chem* 13: 107-242 (1958)). Preferably, fibroin is obtained from a solution containing a dissolved silkworm silk or spider silk. The silkworm silk protein is obtained, for example, from *Bombyx mori*, and the spider silk is obtained from *Nephila clavipes*. In the alternative, the silk proteins suitable for use in the present invention can be obtained from a solution containing a genetically engineered silk, such as from bacteria, yeast, mammalian cells, transgenic animals or transgenic plants. See, for example, WO 97/08315 and U.S. Pat. No. 5,245,012.

The silk fibroin solution to be concentrated can be prepared by any conventional method known to one skilled in the art. For example, *B. mori* cocoons are boiled for about 30 minutes in an aqueous solution. Preferably, the aqueous solution is about 0.02M $Na_2CO_3$. The cocoons are rinsed, for example, with water to extract the sericin proteins and the extracted silk is dissolved in an aqueous salt solution. Salts useful for this purpose include, lithium bromide, lithium thiocyanate, calcium nitrate or other chemicals capable of solubilizing silk. Preferably, the extracted silk is dissolved in about 9-12M LiBr solution. The salt is consequently removed using, for example, dialysis.

The solution is then concentrated using, for example, dialysis against a hygroscopic polymer, for example, PEG, a polyethylene oxide, amylose or sericin.

Preferably, the PEG is of a molecular weight of 8,000-10,000 g/mol and has a concentration of 25-50%. A slide-a-lyzer dialysis cassette (Pierce, MW CO 3500) is preferably used. However, any dialysis system may be used. The dialysis is for a time period sufficient to result in a final concentration of aqueous silk solution between 10-30%. In most cases dialysis for 2-12 hours is sufficient.

The concentrated aqueous solution of the present invention can be processed into hydrogels, foams, films, threads, fibers, meshes, and scaffolds using processes known in the art. See, e.g., Altman, et al., *Biomaterials* 24:401, 2003.

Biocompatible polymers can be added to the silk solution to generate composite matrices in the process of the present invention.

Biocompatible polymers useful in the present invention include, for example, polyethylene oxide (PEO) (U.S. Pat. No. 6,302,848), polyethylene glycol (PEG) (U.S. Pat. No. 6,395,734), collagen (U.S. Pat. No. 6,127,143), fibronectin (U.S. Pat. No. 5,263,992), keratin (U.S. Pat. No. 6,379,690), polyaspartic acid (U.S. Pat. No. 5,015,476), polylysine (U.S. Pat. No. 4,806,355), alginate (U.S. Pat. No. 6,372,244), chitosan (U.S. Pat. No. 6,310,188), chitin (U.S. Pat. No. 5,093,489), hyaluronic acid (U.S. Pat. No. 387,413), pectin (U.S. Pat. No. 6,325,810), polycaprolactone (U.S. Pat. No. 6,337,198), polylactic acid (U.S. Pat. No. 6,267,776), polyglycolic acid (U.S. Pat. No. 5,576,881), polyhydroxyalkanoates (U.S. Pat. No. 6,245,537), dextrans (U.S. Pat. No. 5,902,800), and polyanhydrides (U.S. Pat. No. 5,270,419). Two or more biocompatible polymers can be used.

Silk films can be produced by preparing the concentrated aqueous silk fibroin solution and casting the solution. In one embodiment, the film is contacted with water or water vapor, in the absence of alcohol. The film can then be drawn or stretched mono-axially or biaxially. See, for example, FIGS. 5a and 5b. The stretching of a silk blend film induces molecular alignment of the film and thereby improves the mechanical properties of the film.

In one embodiment, the film comprises from about 50 to about 99.99 part by volume aqueous silk protein solution and from about 0.01 to about 50 part by volume biocompatible polymer e.g., polyethylene oxide (PEO). Preferably, the resulting silk blend film is from about 60 to about 240 µm thick, however, thicker samples can easily be formed by using larger volumes or by depositing multiple layers.

Figure 2:
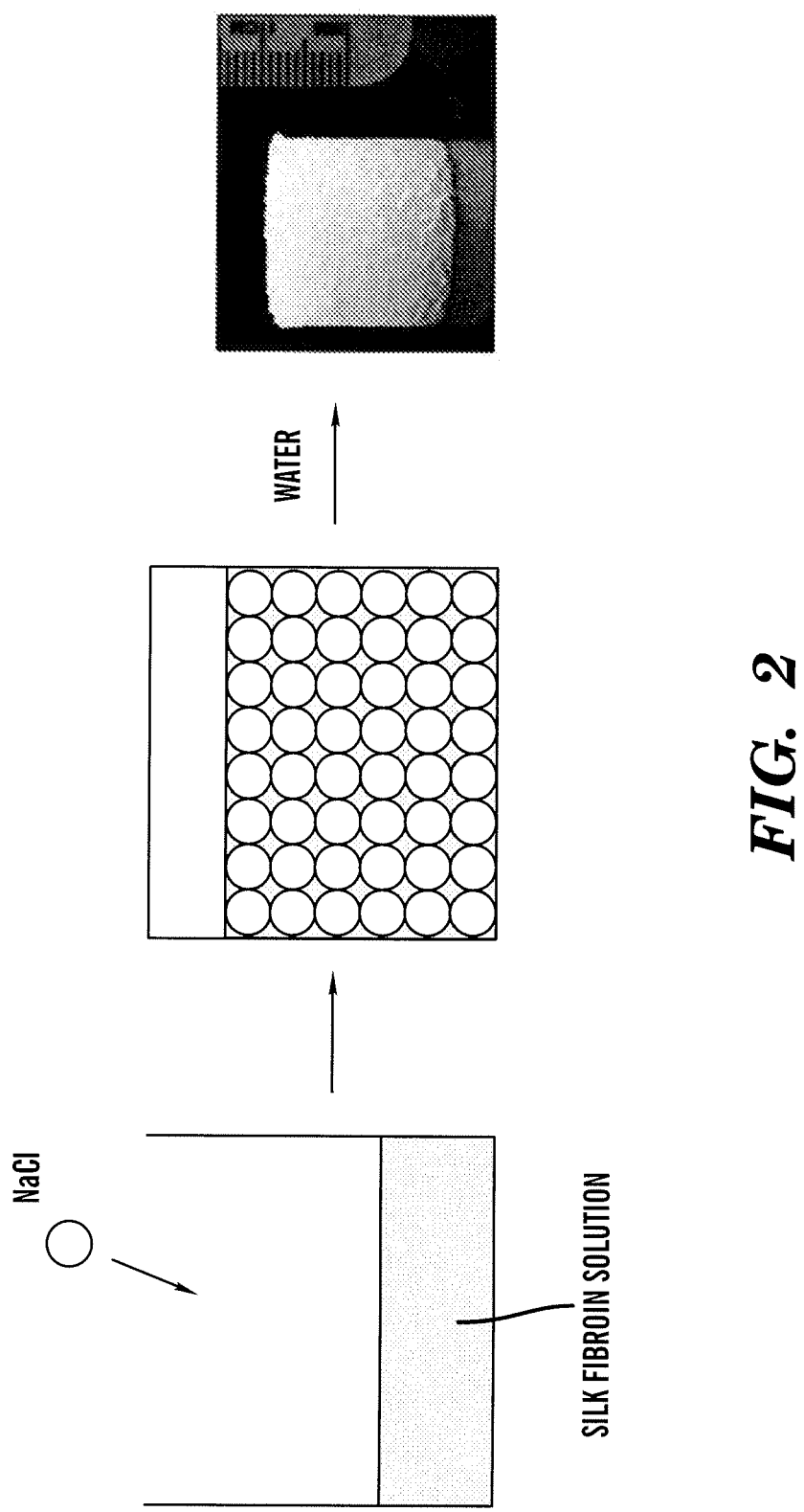
FIG. 2 illustrates one embodiment of the method of the present invention for the preparation of porous silk fibroin scaffolds.

Foams may be made from methods known in the art, including, for example, freeze-drying and gas foaming in which water is the solvent or nitrogen or other gas is the blowing agent, respectively. Alternately the foam is made by contacting the silk fibroin solution with granular salt. The pore size of foams can be controlled, for example by adjusting the concentration of silk fibroin and the particle size of a granular salt (for example, the preferred diameter of the salt particle is between about 50 microns and about 1000 microns). The salts can be monovalent or divalent. Preferred salts are monovalent, such as NaCl and KCl. Divalent salts, such as $CaCl_2$ can also be used. Contacting the concentrated silk fibroin solution with salt is sufficient to induce a conformational change of the amorphous silk to a β-sheet structure that is insoluble in the solution. After formation of the foam, the excess salt is then extracted, for example, by immersing in water. The resultant porous foam can then be dried and the foam can be used, for example, as a cell scaffold in biomedical application. See, FIG. 2.

In one embodiment, the foam is a micropatterned foam. Micropatterned foams can be prepared using, for example, the method set forth in U.S. Pat. No. 6,423,252, the disclosure of which is incorporated herein by reference. The method comprises contacting the concentrated silk solution of the present invention with a surface of a mold, the mold comprising on at least one surface thereof a three-dimensional negative configuration of a predetermined micropattern to be disposed on and integral with at least one surface of the foam, lyophilizing the solution while in contact with the micropatterned surface of the mold, thereby providing a lyophilized, micropatterned foam, and removing the lyophilized, micropatterned foam from the mold. Foams prepared according this method comprise a predetermined and designed micropattern on at least one surface, which pattern is effective to facilitate tissue repair, ingrowth or regeneration.

Fibers may be produced using, for example, wet spinning or electrospinning. Alternatively, as the concentrated solution has a gel-like consistency, a fiber can be pulled directly from the solution.

Electrospinning can be performed by any means known in the art (see, for example, U.S. Pat. No. 6,110,590). Preferably, a steel capillary tube with a 1.0 mm internal diameter tip is mounted on an adjustable, electrically insulated stand. Preferably, the capillary tube is maintained at a high electric potential and mounted in the parallel plate geometry. The capillary tube is preferably connected to a syringe filled with silk solution. Preferably, a constant volume flow rate is maintained using a syringe pump, set to keep the solution at the tip of the tube without dripping. The electric potential, solution flow rate, and the distance between the capillary tip and the collection screen are adjusted so that a stable jet is obtained. Dry or wet fibers are collected by varying the distance between the capillary tip and the collection screen.

A collection screen suitable for collecting silk fibers can be a wire mesh, a polymeric mesh, or a water bath. Alternatively and preferably, the collection screen is an aluminum foil. The aluminum foil can be coated with Teflon fluid to make peeling off the silk fibers easier. One skilled in the art will be able to readily select other means of collecting the fiber solution as it travels through the electric field. As is described in more detail in the Examples section below, the electric potential difference between the capillary tip and the aluminum foil counter electrode is, preferably, gradually increased to about 12 kV, however, one skilled in the art should be able to adjust the electric potential to achieve suitable jet stream.

The present invention additionally provides a non-woven network of fibers comprising a fiber of the present invention. The fiber may also be formed into yarns and fabrics including for example, woven or weaved fabrics.

The fibroin silk solution of the present invention may also be coated onto various shaped articles including biomedical devices (e.g. stents), and silk or other fibers, including fragments of such fibers.

Silk hydrogels can be prepared by methods known in the art, and as exemplified herein. The sol-gel transition of the concentrated silk fibroin solution can be modified by changes in silk fibroin concentration, temperature, salt concentrations (e.g. $CaCl_2$, NaCl, and KCl), pH, hydrophilic polymers, and the like. Before the sol-gel transition, the concentrated aqueous silk solution can be placed in a mold or form. The resulting hydrogel can then be cut into any shape, using, for example a laser.

The materials produced using the present invention, e.g., hydrogels, fibers, films, foams, or meshes, may be used in a variety of medical applications such as a drug (e.g, small molecule, protein, or nucleic acid) delivery device, including controlled release systems, wound closure systems, including vascular wound repair devices, hemostatic dressings, patches and glues, sutures, and in tissue engineering applications, such as, for example, scaffolds for tissue regeneration, ligament prosthetic devices and in products for long-term or bio-degradable implantation into the human body. Films may also be used for a wide range of materials science and engineering needs, such as controlled drug release systems, coatings, composites or as stand alone materials.

Additionally, these biomaterials can be used for organ repair replacement or regeneration strategies that may benefit from these unique scaffolds, including but are not limited to, spine disc, cranial tissue, dura, nerve tissue, liver, pancreas, kidney, bladder, spleen, cardiac muscle, skeletal muscle, tendons, ligaments and breast tissues.

In another embodiment of the present invention, silk biomaterials can contain therapeutic agents. To form these materials, the silk solution is mixed with a therapeutic agent prior to forming the material or loaded into the material after it is formed. The variety of different therapeutic agents that can be used in conjunction with the biomaterials of the present invention is vast and includes small molecules, proteins, peptides and nucleic acids. In general, therapeutic agents which may be administered via the invention include, without limitation: antiinfectives such as antibiotics and antiviral agents; chemotherapeutic agents (i.e. anticancer agents); anti-rejection agents; analgesics and analgesic combinations; anti-inflammatory agents; hormones such as steroids; growth factors (bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-β-III), vascular endothelial growth factor (VEGF)); anti-angiogenic proteins such as endostatin, and other naturally derived or genetically engineered proteins, polysaccharides, glycoproteins, or lipoproteins. Growth factors are described in The Cellular and Molecular Basis of Bone Formation and Repair by Vicki Rosen and R. Scott Thies, published by R. G. Landes Company, hereby incorporated herein by reference. Additionally, the silk biomaterials of the present invention can be used to deliver any type of molecular compound, such as, pharmacological materials, vitamins, sedatives, steroids, hypnotics, antibiotics, chemotherapeutic agents, prostaglandins, and radiopharmaceuticals. The delivery system of the present invention is suitable for delivery the above materials and others including but not limited to proteins, peptides, nucleotides, carbohydrates, simple sugars, cells, genes, anti-thrombotics, anti-metabolics, growth factor inhibitor, growth promoters, anticoagulants, antimitotics, fibrinolytics, anti-inflammatory steroids, and monoclonal antibodies.

Silk biomaterials containing bioactive materials may be formulated by mixing one or more therapeutic agents with the polymer used to make the material. Alternatively, a therapeutic agent could be coated on to the material preferably with a pharmaceutically acceptable carrier. Any pharmaceutical carrier can be used that does not dissolve the silk material. The therapeutic agents, may be present as a liquid, a finely divided solid, or any other appropriate physical form.

The biomaterials described herein can be further modified after fabrication. For example, the scaffolds can be coated with additives, such as bioactive substances that function as receptors or chemoattractors for a desired population of cells. The coating can be applied through absorption or chemical bonding.

Additives suitable for use with the present invention includes biologically or pharmaceutically active compounds. Examples of biologically active compounds include, but are not limited to: cell attachment mediators, such as collagen, elastin, fibronectin, vitronectin, laminin, proteoglycans, or peptides containing known integrin binding domains e.g. "RGD" integrin binding sequence, or variations thereof, that are known to affect cellular attachment (Schaffner P & Dard 2003 Cell Mol Life Sci. January; 60(1):119-32; Hersel U. et al. 2003 Biomaterials. November; 24(24):4385-415); biologically active ligands; and substances that enhance or exclude particular varieties of cellular or tissue ingrowth. For example, the steps of cellular repopulation of a 3-dimensional scaffold matrix preferably are conducted in the presence of growth factors effective to promote proliferation of the cultured cells employed to repopulate the matrix. Agents that promote proliferation will be dependent on the cell type employed. For example, when fibroblast cells are employed, a growth factor for use herein may be fibroblast growth factor (FGF), most preferably basic fibroblast growth factor (bFGF) (Human Recombinant bFGF, UPSTATE Biotechnology, Inc.). Other examples of additive agents that enhance proliferation or differentiation include, but are not limited to, osteoinductive substances, such as bone morphogenic proteins (BMP); cytokines, growth factors such as epidermal growth factor (EGF), platelet-derived growth factor (PDGF), insulin-like growth factor (IGF-I and II) TGF-β, and the like. As used herein, the term additive also encompasses antibodies, DNA, RNA, modified RNA/protein composites, glycogens or other sugars, and alcohols.

The biomaterials can be shaped into articles for tissue engineering and tissue guided regeneration applications, including reconstructive surgery. The structure of the scaffold allows generous cellular ingrowth, eliminating the need for cellular preseeding. The scaffolds may also be molded to form external scaffolding for the support of in vitro culturing of cells for the creation of external support organs.

The scaffold functions to mimic the extracellular matrices (ECM) of the body. The scaffold serves as both a physical support and an adhesive substrate for isolated cells during in vitro culture and subsequent implantation. As the transplanted cell populations grow and the cells function normally, they begin to secrete their own ECM support.

In the reconstruction of structural tissues like cartilage and bone, tissue shape is integral to function, requiring the molding of the scaffold into articles of varying thickness and shape. Any crevices, apertures or refinements desired in the three-dimensional structure can be created by removing portions of the matrix with scissors, a scalpel, a laser beam or any other cutting instrument. Scaffold applications include the regeneration of tissues such as nervous, musculoskeletal, cartilaginous, tendenous, hepatic, pancreatic, ocular, integumenary, arteriovenous, urinary or any other tissue forming solid or hollow organs.

The scaffold may also be used in transplantation as a matrix for dissociated cells, e.g., chondrocytes or hepatocytes, to create a three-dimensional tissue or organ. Tissues or organs can be produced by methods of the present invention for any species.

A number of different cell types or combinations thereof may be employed in the present invention, depending upon the intended function of the tissue engineered construct being produced. These cell types include, but are not limited to: smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells. For example, smooth muscle cells and endothelial cells may be employed for muscular, tubular constructs, e.g., constructs intended as vascular, esophageal, intestinal, rectal, or ureteral constructs; chondrocytes may be employed in cartilaginous constructs; cardiac muscle cells may be employed in heart constructs; hepatocytes and bile duct cells may be employed in liver constructs; epithelial, endothelial, fibroblast, and nerve cells may be employed in constructs intended to function as replacements or enhancements for any of the wide variety of tissue types that contain these cells. In general, any cells may be employed that are found in the natural tissue to which the construct is intended to correspond. In addition, progenitor cells, such as myoblasts or stem cells, may be employed to produce their corresponding differentiated cell types. In some instances it may be preferred to use neonatal cells or tumor cells.

Cells can be obtained from donors (allogenic) or from recipients (autologous). Cells can also be of established cell culture lines, or even cells that have undergone genetic engineering. Pieces of tissue can also be used, which may provide a number of different cell types in the same structure.

Appropriate growth conditions for mammalian cells are well known in the art (Freshney, R. I. (2000) Culture of Animal Cells, a Manual of Basic Technique. Hoboken N.J., John Wiley & Sons; Lanza et al. Principles of Tissue Engineering, Academic Press; 2nd edition May 15, 2000; and Lanza & Atala, Methods of Tissue Engineering Academic Press; 1st edition October 2001). Cell culture media generally include essential nutrients and, optionally, additional elements such as growth factors, salts, minerals, vitamins, etc., that may be selected according to the cell type(s) being cultured. Particular ingredients may be selected to enhance cell growth, differentiation, secretion of specific proteins, etc. In general, standard growth media include Dulbecco's Modified Eagle Medium, low glucose (DMEM), with 110 mg/L pyruvate and glutamine, supplemented with 10-20% fetal bovine serum (FBS) or calf serum and 100 U/ml penicillin are appropriate as are various other standard media well known to those in the art. Growth conditions will vary dependent on the type of mammalian cells in use and tissue desired.

In one embodiment, methods are provided for producing bone or cartilage tissue in vitro comprising culturing multipotent cells on a porous silk fibroin scaffold under conditions appropriate for inducing bone or cartilage formation. Suitable conditions for the generation of bone and cartilage are well known to those skilled in the art. For example, conditions for the growth of cartilage tissue often comprise nonessential amino acids, ascorbic acid-2-phosphate, dexamethasone, insulin, and TGF-$\beta$1. In one preferred embodiment, the nonessential amino acids are present at a concentration of 0.1 mM, ascorbic acid-2-phosphate is present at a concentration of 50 ug/ml, dexamethasone is present at a concentration of 10 nM, insulin is present at a concentration of 5 ug/ml and TGF-$\beta$1 is present at a concentration of 5 ng/ml. Suitable conditions for the growth of bone often include ascorbic acid-2-phosphate, dexamethasone, $\beta$-glycerolphoasphate and BMP-2. In a preferred embodiment, ascorbic acid-2-phosphate is present at a concentration of 50 ug/ml, dexamethasone is present at a concentration of 10 nM, $\beta$-glycerolphoasphate is present at a concentration of 7 mM and BMP-2 is present at a concentration of 1 ug/ml.

In general, the length of the growth period will depend on the particular tissue engineered construct being produced. The growth period can be continued until the construct has attained desired properties, e.g., until the construct has reached a particular thickness, size, strength, composition of proteinaceous components, and/or a particular cell density. Methods for assessing these parameters are known to those skilled in the art.

Following a first growth period the construct can be seeded with a second population of cells, which may comprise cells of the same type as used in the first seeding or cells of a different type. The construct can then be maintained for a second growth period which may be different in length from the first growth period and may employ different growth conditions. Multiple rounds of cell seeding with intervening growth periods may be employed.

In one preferred embodiment, tissues and organs are generated for humans. In other embodiments, tissues and organs are generated for animals such as, dogs, cats, horses, monkeys, or any other mammal.

The cells are obtained from any suitable donor, either human or animal, or from the subject into which they are to be implanted. As used herein, the term "host" or "subject" includes mammalian species, including, but not limited to, humans, monkeys, dogs, cows, horses, pigs, sheep, goats, cats, mice, rabbits, rats.

The cells that are used for methods of the present invention should be derived from a source that is compatible with the intended recipient. The cells are dissociated using standard techniques and seeded onto and into the scaffold. In vitro culturing optionally may be performed prior to implantation. Alternatively, the scaffold is implanted into the subject, allowed to vascularize, then cells are injected into the scaffold. Methods and reagents for culturing cells in vitro and implantation of a tissue scaffold are known to those skilled in the art.

Cells can be seeded within the matrix either pre- or post matrix formation, depending on the method of matrix formation. Uniform seeding is preferable. In theory, the number of cells seeded does not limit the final tissue produced, however optimal seeding may increase the rate of generation. The number of seeded cells can be optimized using dynamic seeding (Vunjak-Novakovic et al. Biotechnology Progress 1998; Radisic et al. Biotechnoloy and Bioengineering 2003).

It is another aspect of the invention that the 3-dimensional porous silk scaffold, described herein, can itself be implanted in vivo and serve as tissue substitute (e.g. to substitute for bone or cartilage). Such implants, would require no seeding of cells, but contain an addition e.g., RGD, that attracts cells.

In one embodiment, silk matrix scaffolds are seeded with multipotent cells in the presence of media that induces either bone or cartilage formation. Suitable media for the production of cartilage and bone are well known to those skilled in the art.

As used herein, "multipotent" cells have the ability to differentiate into more than one cell type in response to distinct differentiation signals. Examples of multipotent cells include, but are not limited to, bone marrow stromal cells (BMSC) and adult or embryonic stem cells. In a preferred embodiment BMSCs are used. BMSCs are multipotential cells of the bone marrow which can proliferate in an undifferentiated state and with the appropriate extrinsic signals, differentiate into cells of mesenchymal lineage, such as cartilage, bone, or fat (Friedenstein, A. J. 1976. Int Rev Cytol 47:327-359; Friedenstein et al. 1987. Cell Tissue Kinet 20:263-272; Caplan, A. I. 1994. Clin Plast Surg 21:429-435; Mackay et al. 1998. Tissue Eng 4:415-428; Herzog et al. Blood. 2003 Nov. 15; 102(10):3483-93. Epub 2003 Jul. 31).

The formation of cartilaginous tissue or bone can be monitored by assays well known to those in the art including, but not limited to, histology, immunohistochemistry, and confocal or scanning electron microscopy (Holy et al., J. Biomed. Mater. Res (2003) 65A:447-453).

Using silk based scaffolds, organized tissue with a predetermined form and structure can be produced either in vitro or in vivo. For example, tissue that is produced ex vivo is functional from the start and can be used as an in vivo implant. Alternatively, the silk based structure can be seeded with cells capable of forming either bone or cartilage and then implanted as to promote growth in vivo. Thus, the scaffolds can be designed to form tissue with a "customized fit" that is specifically designed for implantation in a particular patient. For example, cartilaginous tissue or bone tissue produced by methods of the present invention can be used to replace large cartilage or bone defects found in musculoskeletal disorders and degenerative diseases such as osteoarthritis or rheumatism. Engineered bone and cartilage are also suitable for spine and joint replacements such as, elbow, knee, hip or finger joints or can be used in osteochondral implants.

All biomaterials of the present intention may be sterilized using conventional sterilization process such as radiation based sterilization (i.e. gamma-ray), chemical based sterilization (ethylene oxide), autoclaving, or other appropriate procedures. Preferably the sterilization process will be with ethylene oxide at a temperature between 52-55° C. for a time of 8 hours or less. After sterilization the biomaterials may be packaged in an appropriate sterilize moisture resistant package for shipment and use in hospitals and other health care facilities.

Unless otherwise defined, all technical and scientific terms used herein have the same meaning as commonly understood by one of ordinary skill in the art. Although methods and materials similar or equivalent to those described herein can be used in the practice or testing of the invention, the preferred methods and materials are described below. All publications, patent applications, patents and other references mentioned herein are incorporated by reference. In addition, the materials, methods and examples are illustrative only and not intended to be limiting. In case of conflict, the present specification, including definitions, controls.

The invention will be further characterized by the following examples which are intended to be exemplary of the invention.

EXAMPLES

Example I

Preparation of Pure Silk Fibers from Water from Regenerated Silk Solution by Electrospinning Methods
Preparation of a Regenerated B. mori Silk Fibroin Solution B. mori silk fibroin was prepared as follows as a modification of our earlier procedure (Sofia, et al., *Journal of Biomedical Materials Research* 2001, 54, 139-148). Cocoons were boiled for 30 min in an aqueous solution of 0.02M $Na_2CO_3$, then rinsed thoroughly with water to extract the glue-like sericin proteins. The extracted silk was then dissolved in 9.3M LiBr solution at room temperature yielding a 20% (w/v) solution. This solution was dialyzed in water using a Slide-a-Lyzer dialysis cassette (Pierce, MWCO 2000) for 48 hours. The final concentration of aqueous silk solution was 8.0 wt %, which was determined by weighing the remaining solid after drying.

This solution was concentrated further by exposure to an aqueous polyethylene glycol (PEG) (MW 8,000 to 10,000) solution (25-50 wt %) on the outside of a Slide-a-Lyzer dialysis cassette (Pierce, MWCO 3500) for 2 to 12 hrs by osmotic pressure (FIG. 1). The final concentration of aqueous silk solution could be formed to between 10-30 wt % or greater.

Electrospinning

In order to increase the viscosity of aqueous silk solution above 8 wt % for spinning, the solution was concentrated using the PEG solution method as described above. This was required since the viscosity and surface tension of the pure silk solution (8 wt %) was not high enough to maintain a stable drop at the end of the capillary tip. The increase of silk solutions generated a viscosity and surface tension suitable for electrospinning. With the new more concentrated pure silk solutions (10-30%), direct spinning is now feasible. The distance between the tip and the collector was 10-15 cm and flow rate of the fluid was 0.01 to 0.05 ml/min. As the potential difference between the capillary tip and the aluminum foil counter electrode was gradually increased 30 kV (E=2-3 kV/cm), the drop at the end of the capillary tip elongated from a hemispherical shape into a cone shape. The morphology and diameters of the electrospun fibers were examined using SEM. Silk/PEO blend solution produced microsize fibers with diameters 1.5 µm to 25 µm. The morphology of fiber surface and fracture surface in liquid nitrogen was well matched with native silk fiber.

Example II

Preparation of Silk Fibroin Scaffolds

Porous three-dimensional scaffolds were prepared from silk fibroin aqueous solutions by salt-leaching. By adjusting the concentration of silk fibroin and the particle size of granular NaCl, the morphological and functional properties of the scaffolds could be controlled. The scaffolds had highly homogeneous and interconnected pores and showed pore sizes ranging from 470 to 940 um depending on the mode of preparation. The scaffolds had porosities >90%. The compressive strength and modulus of scaffolds was up to 320±10 KPa and 3330±500 KPa, respectively. The scaffolds were fully degraded by protease during 21 days. These new silk-based 3-D matrices provide useful properties as biomaterial matrices for tissue engineering due to the all-aqueous mode of preparation, control of pore size, connectivity of pores, degradability and useful mechanical features.

Methods

Preparation of Silk Fibroin Aqueous Solution

Cocoons of *B. mori* were boiled for 20 min in an aqueous solution of 0.02M $Na_2CO_3$, and then rinsed thoroughly with distilled water to extract the glue-like sericin proteins and wax. The extracted silk fibroin was then dissolved in 9.3M LiBr solution at 60° C. for 4 hrs, yielding a 20 w/v % solution. This solution was dialyzed in distilled water using a Slide-a-Lyzer dialysis cassette (MWCO 3500, Pierce) for 2 days. The final concentration of silk fibroin aqueous solution was ca. 8 w/v %, which was determined by weighing the remaining solid after drying. To prepare concentrated silk fibroin solution, 10 ml of 8 w/v % silk fibroin solution was dialyzed against 1 liter of 25 wt % polyethylene glycol (PEG, 10,000 g/mol) solution at room temperature by using Slide-a-Lyzer dialysis cassettes (MWCO 3500). After the required time, the concentrated silk fibroin solution was slowly collected by syringe to avoid excessive shearing and the concentration was determined. Silk fibroin aqueous solutions with concentration less than 8 wt % were prepared by diluting with distilled water. All solutions were stored at 7° C. before use to avoid premature precipitation. Silk fibroin films prepared from 8 w/v % solutions were evaluated to verify the removal of $Li^+$ ion by XPS; no residual $Li^+$ ion was detected.

Preparation of Silk Fibroin Scaffolds

Four grams of granular NaCl (particle size; 300~1180 um) were added to 2 ml of silk fibroin aqueous solution (4~10 wt %) in disk-shaped Teflon containers (FIG. 2a). The container was covered and left at room temperature. After 24 hrs, the container was immersed in water and the NaCl was extracted for 2 days. The porous silk fibroin scaffolds formed in this process were stored in water at 7° C. before use.

X-Ray Diffraction

X-ray diffraction of freeze-dried samples of the scaffold were obtained with Ni-filtered Cu-Kα radiation (λ=0.15418 nm) from a Rigaku RU-200BH rotating-anode X-ray generator operating at 40 kV and 40 mA. X-ray diffraction patterns were recorded with a point collimated beam and a imaging plate (Fuji Film BAS-IP SR 127) in an evacuated camera. The camera length was calibrated with NaF (d=0.23166 nm).

FTIR Spectroscopy

Approximately 1 mg of freeze-dried sample was pressed into a pellet with 200 mg of potassium bromide and Fourier transform infrared (FTIR) spectrum was recorded with an accumulation of 64 scans and a resolution of 4 cm-1 by Nicolet Magna 860.

Scanning Electron Microscopy (SEM)

Silk scaffolds were cut into sections in distilled water using a razor blade and then freeze-dried. Samples were sputter coated with gold. The morphology of scaffolds was observed with a LEO Gemini 982 Field Emission Gun SEM. Pore size was obtained using ImageJ software developed at the US National Institutes of Health.

Porosity

The density and porosity of the silk scaffolds were measured by liquid displacement (Zhang, R. Y., et al., J. Biomed. Mater. Res. 1999, 44, 446-455). Hexane was used as the displacement liquid as it permeates through silk scaffolds without swelling or shrinking the matrix. The silk scaffold (dry weight, W) was immersed in a known volume (V1) of hexane in a graduated cylinder for 5 min. The total volume of hexane and the hexane-impregnated scaffold was recorded as V2. The hexane-impregnated scaffold was then removed from the cylinder and the residual hexane volume was recorded as V3. The total volume of the scaffold was:

$$V=(V2-V1)+(V1-V3)=V2-V3.$$

V2−V1 is the volume of the polymer scaffold and V1−V3 is the volume of hexane within the scaffold. The porosity of the scaffold (ε) was obtained by:

$$\varepsilon(\%)=(V1-V3)/(V2-V3)\times 100$$

Swelling Properties

Silk fibroin scaffolds were immersed in distilled water at room temperature for 24 hrs. After excess water was removed, the wet weight of the scaffold (Ws) was determined. Samples were then dried in an oven at 65° C. under vacuum overnight and the dry weight of scaffolds (Wd) was determined. The swelling ratio of the scaffold and the water content in the scaffold were calculated as follows:

$$\text{Swelling ratio}=(Ws-Wd)/Wd$$

$$\text{Water uptake }(\%)=[(Ws-Wd)/Ws]\times 100$$

Mechanical Properties

Resistance to mechanical compression of the scaffolds (12 mm diameter, 10 mm height, disks) were performed on an Instron 8511 equipped with a 0.1 KN load cell at room temperature. The crosshead speed was 10 mm/min. The compression tests were conducted conventionally as an open-sided/confined method. Four samples were evaluated for each composition. Cylinder-shaped samples measuring 12 mm in diameter and 10 mm in height were used, according to a modification based on the ASTM method F451-95. The compressive stress and strain were graphed and the average compressive strength as well as the compressive modulus and standard deviation determined. The elastic modulus was defined by the slope of the initial linear section of the stress-strain curve. The compressive strength was determined by drawing a line parallel to this, starting at 1% strain. The point at which this line crossed the stress-strain curve was defined as the compressive strength of the foam (Thomson R C et al., *Biomaterials* 1998, 19; 1935-1943).

In Vitro Enzymatic Degradation

The degradation of the silk fibroin scaffolds was evaluated using protease XIV (EC 3.4.24.31, Sigma-Aldrich) with an activity of 5.6 U/mg. Samples (12 mm diameter, 5 mm height) were immersed in 5 ml of phosphate buffer saline (pH 7.4) containing protease (1 U) at 37° C. After the specific time samples were washed with phosphate buffer saline and distilled water, and freeze-dried. The enzyme solution was replaced with newly prepared solution every 24 hrs. For controls, samples were immersed in phosphate buffer saline without enzyme.

Results and Discussion

Preparation of Water-Based Scaffolds

Porous silk fibroin scaffolds were prepared using a salt-leaching method that has been previously used in the preparation of porous scaffolds from other polymers such as collagen and polylactic acid. The pore size and the porosity of the scaffolds were regulated by the addition of granular NaCl with particle sizes of diameter 300 to 1180 μm to the silk fibroin aqueous solution. In this process, some of the surface of the NaCl particles dissolved in the silk fibroin aqueous solution, while most of the salt was retained as solid particles because of saturation of the solution. The silk fibroin aqueous solutions formed into hydrogels in the mixture after ~24 hrs, which resulted in the formation of water-stable porous matrices. Table 1 shows the silk fibroin concentrations and particle sizes of NaCl used in the study. With an increase in silk fibroin concentration, matrices were homogeneously formed through the use of larger particle sizes of the NaCl. When NaCl with particle sizes of 500 to 600 μm were added to 8 wt % silk fibroin solution, the surface of the silk fibroin aqueous solutions rapidly formed a hydrogel.

TABLE 1

Preparation of scaffolds from various silk fibroin concentrations and particle sizes of NaCl.

| Particle size of sodium chloride (μm) | Silk fibroin concentration (w/v %) | | | |
|---|---|---|---|---|
| | 4 | 6 | 8 | 10 |
| 1000~1180 | o | o | o | o |
| 850~1000 | o | o | o | Δ |
| 710~850 | o | o | o | x |
| 600~700 | o | o | Δ | x |
| 500~600 | o | Δ | x | x |
| 425~500 | Δ | x | x | x |
| 300~425 | x | x | x | x | degree of homogeneity: o > Δ > x

In concentrated salt solutions, solvating forces are significantly altered from those in dilute electrolyte solutions because salt ions change the structure of the intervening water (Curtis R A et al., *Biophys Chem* 2002, 98:249-265). The effect of concentrated salt solutions with chloride ion, such as NaCl, KCl, $CaCl_2$ and $MgCl_2$, on silk fibroin was determined at salt concentrations up to 3M at room temperature. When a drop of silk fibroin solution (8 wt %) was added to concentrated salt solutions of 3M, silk hydrogels formed immediately in the NaCl and KCl solutions but not in the $CaCl_2$ and $MgCl_2$ solutions. Ions are classified as kosmotropic or chaotropic, based on their size and charge (Grigsby J J et al., *Biophys Chem* 2001, 91:231-243). Ions with high charge density such as $Ca^{2+}$ and $Mg^{2+}$ are highly kosmotropic, and ions with low charge density such as $K^+$ are chaotropic. $Na^+$ is weakly kosmotropic and is weakly chaotropic. Kosmotropic ions bind adjacent water molecules more strongly than chaotropic ions. In addition, kosmotropic ions strongly interact with oppositely charged residues on the protein surface due to their high charge density. At low salt concentration, the solution contains a sufficient number of water molecules to hydrate both the protein surface and the ions. At higher salt concentrations, more water molecules are needed to hydrate the increasing number of ions. Therefore water molecules are easily removed from the proteins as concentrations of salt solutions increase.

From the primary sequence of the silkworm silk fibroin heavy chain, seven internal hydrophobic blocks and seven much smaller internal hydrophilic blocks, with two large hydrophilic blocks at the chain ends are present (Zhou, C. Z., et al., Nucleic Acids Res. 2000, 28, 2413-2419). The percentage of hydrophobic residues in silk fibroin is 79% (Braun, F. N., et al., Int. J. Biol. Macromol. 2003, 32, 59-65) and the repetitive sequence in these hydrophobic blocks consists of GAGAGS (SEQ ID NO: 4) peptides that dominate the β-sheet structure that forms the crystalline regions in silk fibroin fibers and films (Mita, K., et al., J. Mol. Evol. 1994, 38, 583-592).

Since protein solubility typically decreases as salt concentration rises, interactions between proteins become favored (Curtis, R. A., et al., Biophys. Chem. 2002, 98, 249-265). It is well known that the hydrophobic interactions between non-polar residues increase with addition of salt, leading to the salting-out effect (Robinson, D. R., et al., J. Am. Chem. Soc. 1965, 87, 2470-2479). The behavior of the fibroin in the salt system described may be related to the role of the salt ions in extracting water that would otherwise coat the hydrophobic fibroin domains, promoting chain-chain interactions leading to the new more stable structure. These hydrophobic interactions induce protein folding, resulting in β-sheet formation (Li, G. Y., et al., Biochem. 2001, 268, 6600-6606).

Alginate or glass beads were examined to further clarify the ion effects on hydrogelation of silk fibroin (8 wt %). While gelation time of silk fibroin with glass beads showed a similar result as that observed over 30 days with silk fibroin in a previous study (Kim U J et al., *Biomacromolecules*, in press), the gelation time of the silk fibroin solution with alginate beads was ~2 times faster due, presumably due to the removal of water molecules from the proteins associated with the swelling of the alginate beads. Compared with the gelation time (24 hrs) of silk fibroin in saturated NaCl solution, salt ions strongly induced protein-protein interactions.

Structural Analysis

Figure 3B:
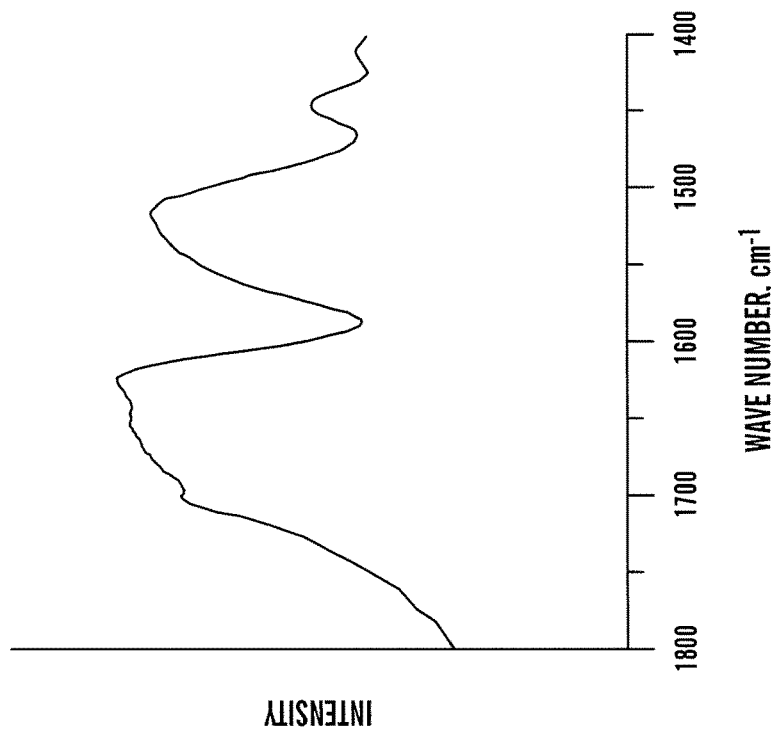
FIGS. 3a and 3b show (FIG. 3a) X-ray diffraction and (FIG. 3b) FTIR spectrum of a silk fibroin scaffold prepared by the water-based method described in Example II.
Figure 3A:
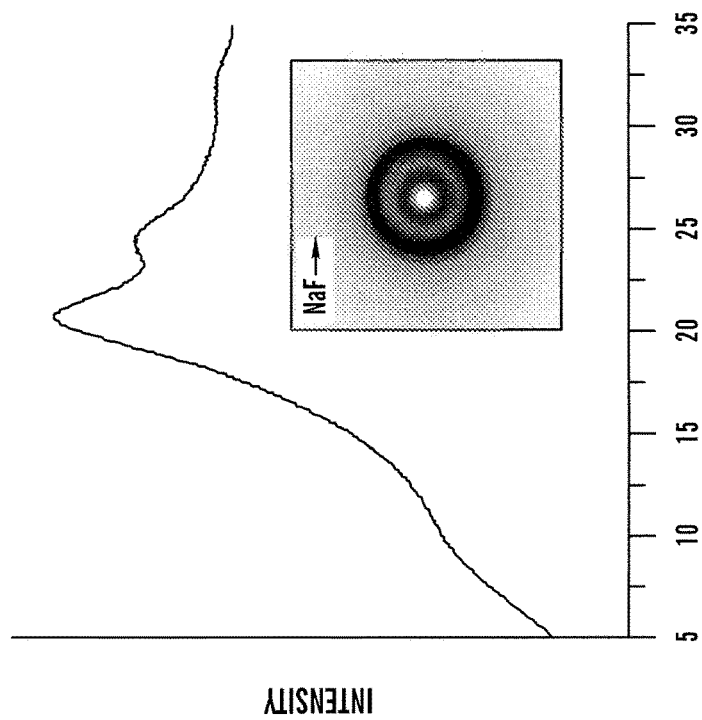

Structural changes in the silk fibroin were determined by X-ray diffraction and FTIR (FIG. 3). X-ray diffraction of silk fibroin scaffolds showed a distinct peak at 20.8° and a minor peak and 24.6°. These peaks were almost the same as those of the β-sheet crystalline structure (silk II) of native silk fibroin (Asakura, T., et al., Macromolecules 1985, 18, 1841-1845). The results indicate a β-crystalline spacing distances of 4.3 and 3.6 Å according to the 20.8° and 24.6° reflections, respectively. FTIR spectra of silk fibroin scaffolds showed characteristic peaks of silk II at 1701 $cm^{-1}$ and 1623 $cm^{-1}$ (amide I) (Asakura, T., et al., Macromolecules 1985, 18, 1841-1845). Silk fibroin in aqueous solution at neutral pH exhibited a random coil conformation. From the results of the X-ray diffraction and FTIR analyses, the formation of silk fibroin scaffolds from these solutions induced a conformational transition from random coil to β-sheet.

Morphology

SEM images of freeze-dried scaffolds prepared from various silk fibroin concentrations and various sized particles of NaCl showed highly interconnected porous structures and the pore distribution was homogeneous in the whole scaffolds except for a thin layer formed on the top surface of the scaffolds, the air-water interface. The scaffolds showed rough pore surfaces highly interconnected by a number of smaller pores. Globular-like structures, 1~3 μm in diameter, were observed on the surfaces of the pores. With an increase in silk fibroin concentration, the pore walls were thicker. Table 2 shows actual pore sizes in the scaffolds, ranging from 350 to 920 μm.

TABLE 2

Measured pore sizes (μm) of silk fibroin scaffolds.

| Particle size of sodium chloride (μm) | Silk fibroin concentration (w/v %) | | | |
|---|---|---|---|---|
| | 4 | 6 | 8 | 10 |
| 1000~1180 | 940 ± 50 | 930 ± 40 | 920 ± 50 | 920 ± 50 |
| 850~1000 | 760 ± 30 | 750 ± 50 | 750 ± 20 | — |
| 710~850 | 650 ± 30 | 650 ± 50 | 640 ± 30 | — |
| 600~700 | 570 ± 30 | 550 ± 30 | — | — |
| 500~600 | 470 ± 30 | — | — | — |

Values are average ± standard derivation (N = 20).

The actual pore sizes in the scaffolds were 80~90% smaller than the particle size of NaCl used in the process. The pore sizes in scaffolds prepared with the same particle size of NaCl, regardless of the concentration of silk fibroin used, resulted in similar sized pores.

Porosity and Swelling Properties

Silk fibroin scaffolds with >90% porosity were formed and porosities increased with a decrease in pore size and silk fibroin concentrations (Table 3). These values were similar as those (84~98%) of HFIP-derived silk scaffolds prepared by salt leaching or gas forming (Nazarov R, et al., *Biomacromolecules*, in press). Swelling ratio and water uptake of the scaffolds are shown in Tables 4 and 5.

TABLE 3

Porosity (%) of silk fibroin scaffolds

| Particle size of sodium chloride (μm) | Silk fibroin concentration (w/v %) | | | |
|---|---|---|---|---|
| | 4 | 6 | 8 | 10 |
| 1000~1180 | 95 ± 1.8 | 93 ± 0.7 | 92 ± 1.3 | 85 ± 1.5 |
| 850~1000 | 95 ± 1.5 | 95 ± 0.2 | 94 ± 0.2 | — |
| 710~850 | 97 ± 0.4 | 96 ± 1.6 | 95 ± 1.5 | — |
| 600~700 | 97 ± 1.6 | 97 ± 0.6 | — | — |
| 500~600 | 97 ± 0.5 | — | — | — |

Values are average ± standard derivation (N = 3).

TABLE 4

Swelling ratio of silk fibroin scaffolds.

| Particle size of sodium chloride (μm) | Silk fibroin concentration (w/v %) | | | |
|---|---|---|---|---|
| | 4 | 6 | 8 | 10 |
| 1000~1180 | 55.3 ± 3.8 | 36.1 ± 0.1 | 23.6 ± 1.2 | 19.2 ± 4.3 |
| 850~1000 | 50.0 ± 0.2 | 29.8 ± 0.6 | 21.5 ± 1.9 | — |
| 710~850 | 48.6 ± 2.0 | 28.9 ± 1.5 | 19.8 ± 0.2 | — |
| 600~700 | 46.8 ± 2.6 | 28.4 ± 2.7 | — | — |
| 500~600 | 47.6 ± 2.1 | — | — | — |

Values are average ± standard derivation (N = 3).

TABLE 5

Water uptake (%) of silk fibroin scaffolds.

| Particle size of sodium chloride (μm) | Silk fibroin concentration (w/v %) | | | |
|---|---|---|---|---|
| | 4 | 6 | 8 | 10 |
| 1000~1180 | 98.2 ± 0.1 | 97.3 ± 0.1 | 95.9 ± 0.2 | 94.9 ± 1.0 |
| 850~1000 | 98.0 ± 0.1 | 96.8 ± 0.1 | 95.2 ± 0.1 | — |
| 710~850 | 98.0 ± 0.1 | 96.7 ± 0.2 | 95.6 ± 0.4 | — |
| 600~700 | 97.9 ± 0.1 | 96.6 ± 0.3 | — | — |
| 500~600 | 97.9 ± 0.1 | — | — | — |

Values are average ± standard derivation (N = 3).

Swelling ratio decreased gradually with a decrease in pore size. However, swelling ratio decreased significantly with an increase in silk fibroin concentration due to the decrease in porosity. The swelling ratio of the scaffold prepared from 8 wt % silk fibroin was ~8 times lower than that of collagen scaffolds, due to the differences in the hydrophilicities of proteins (Ma L. et al., *Biomaterials* 2003, 24:4833-4841). The value was similar to polylactic acid scaffolds (Maquet V. et al., *Biomaterials* 2004, 25:4185-4194). Water uptake of the scaffolds in distilled water was >93% during 24 hrs. The high water-binding ability of the scaffolds can be attributed to the highly porous structure of the protein network.

Mechanical Properties

The scaffolds exhibited a ductile and sponge-like behavior with different stiffness depending on the concentration of silk fibroin used in the process. An elastic region was observed at initial strain followed by a peak stress. Table 6 shows the mechanical properties of the silk fibroin scaffolds. The compressive strength and modulus of the scaffolds increased with an increase in silk fibroin concentration.

TABLE 6

Mechanical properties of silk fibroin scaffolds

| Particle size of sodium chloride (μm) | Silk fibroin concentration (w/v %) | | | | | | | |
|---|---|---|---|---|---|---|---|---|
| | 4 | | 6 | | 8 | | 10 | |
| | Compressive stress (kPa) | Compressive modulus (kPa) | Compressive stress (kPa) | Compressive modulus (kPa) | Compressive stress (kPa) | Compressive modulus (kPa) | Compressive stress (kPa) | Compressive modulus (kPa) |
| 1000~1180 | 11 ± 3 | 70 ± 5 | 49 ± 4 | 560 ± 50 | 100 ± 10 | 1300 ± 40 | 320 ± 10 | 3330 ± 500 |
| 850~1000 | 11 ± 1 | 80 ± 5 | 54 ± 8 | 620 ± 40 | 125 ± 10 | 1530 ± 190 | — | — |
| 710~850 | 12 ± 1 | 100 ± 5 | 58 ± 3 | 670 ± 30 | 140 ± 15 | 1940 ± 240 | — | — |
| 600~700 | 13 ± 3 | 115 ± 10 | 60 ± 5 | 770 ± 50 | — | — | — | — |
| 500~600 | 13 ± 3 | 130 ± 10 | — | — | — | — | — | — |

Values are average ± standard derivation (N = 4).

The improvement in mechanical properties was attributed to the increase in polymer concentration accompanied with the increase in the wall thickness of the pores. At the same silk fibroin concentration, scaffolds prepared with smaller particle sizes of NaCl showed higher compressive strength and modulus due to the decreased pore size. It is considered that the increased pore wall sites induced by the decreased pore size provided more paths to distribute the applied stress. The increased pore sites may functioned as a barrier, such as crack disipation, to reduce crack propagation. In addition, it has been reported that a more uniform pore distribution improved the mechanical properties of polymer matrices. Therefore, stress applied to porous materials is concentrated at the pore interface, and if the pore distribution is not uniform, polymer matrices typically deform at a lower stress (Harris L D. Et al., *J Biomed Mater Res* 1998, 42:396-402). For example, in our recent studies (Nazarov R. et al., *Biomacromolecules*, in press). three-dimensional silk fibroin scaffolds were developed using a salt leaching method with HFIP. While these scaffolds had smaller pore size and utilized a higher concentration of silk fibroin in processing, the compressive strengths (30 to 250 KPa) of the HFIP-derived silk scaffolds (17 wt % silk in HFIP) prepared by salt leaching were similar to those found for the aqueous-derived (8~10 wt % silk in water) silk scaffolds in the present study. However, the compressive modulus of aqueous-derived silk scaffolds was 3~4 times higher (100 to 790 kPa) for the HFIP-derived silk scaffolds.

Enzymatic Degradation

Figure 4B:
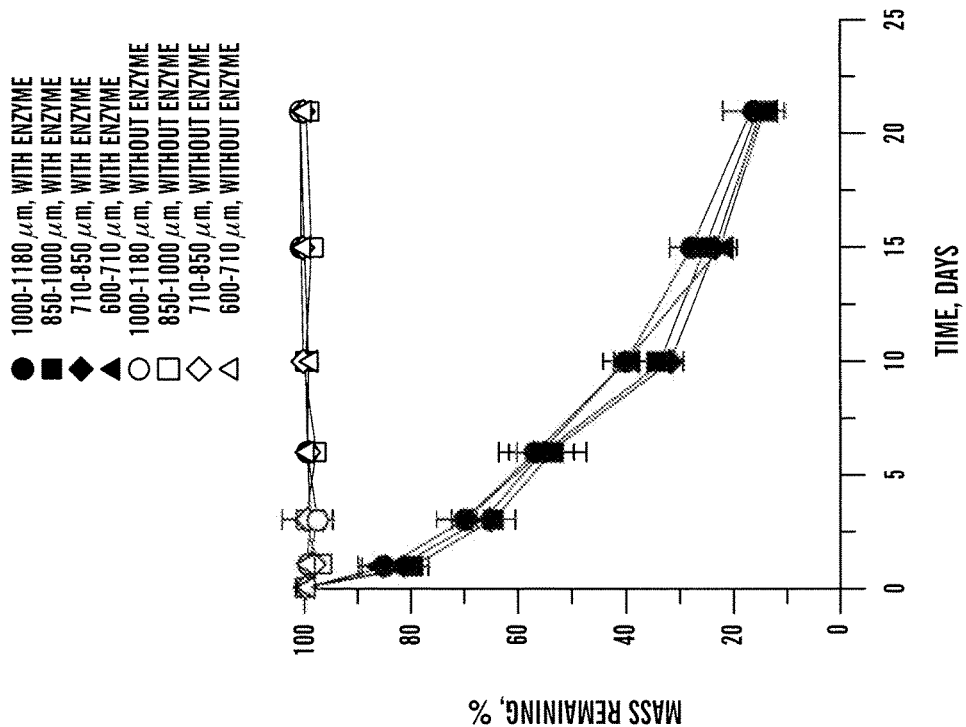
FIGS. 4a and 4b shown the mass of scaffolds remaining over time when prepared from (FIG. 4a) 4 or 8 wt % silk fibroin with NaCl of 850-1000 μm diameter particle size, and (FIG. 4b) of the scaffolds prepared with 6 wt % prepared with various particle sizes of NaCl.
Figure 4A:
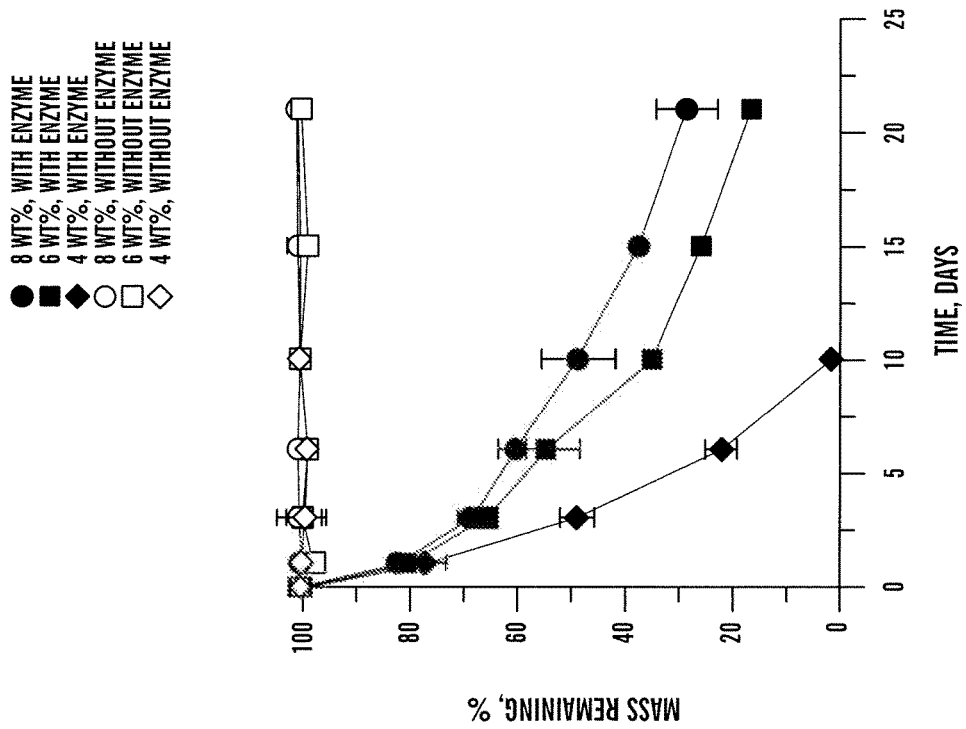

FIG. 4a shows the mass of the scaffolds over time prepared from 4 to 8 wt % silk fibroin with NaCl of 850-1000 μm diameter particle sizes during a degradation period of 21 days. The scaffolds in phosphate buffer without protease showed no degradation within 21 days. The scaffolds prepared with 4 wt % fibroin rapidly degraded and the mass remaining was only 2% after 10 days. The scaffolds prepared from 6 and 8 wt % fibroin gradually degraded with time and the mass was reduced to 30 and 20%, respectively, after 21 days. FIG. 4b shows the mass of the scaffolds remaining when prepared from 6 wt % silk fibroin with various particle sizes of NaCl. The degradation patterns suggest that pore size did not correlate with degradation rate, on the nature of the initial concentration of fibroin.

Conclusions

Porous silk fibroin scaffolds were prepared directly from silk fibroin aqueous solutions by a salt leaching method, in the complete absence of any organic solvents or chemical crosslinking. The formation of the scaffolds included a structural transition from random coil to β-sheet. This transition provides a mechanistic basis for the transition, as the salt may promote water loss from the hydrophobic domains leading to enhanced chain-chain interactions and thus β-sheet formation. Functional and morphological properties of the scaffolds were controlled by the concentration of the silk fibroin solution used in the process and the particle size of NaCl.

Example III

Preparation of Silk Hydrogels

Control of silk fibroin concentration in aqueous solutions via osmotic stress was studied to assess relationships to gel formation and structural, morphological and functional (mechanical) changes associated with this process. Environmental factors potentially important in the in vivo processing of aqueous silk fibroin were also studied to determine their contributions to this process. Gelation of silk fibroin aqueous solutions was affected by temperature, $Ca^{2+}$, pH and polyethylene oxide (PEO). Gelation time decreased with increase in protein concentration, decrease in pH, increase in temperature, addition of $Ca^{2+}$ and with the addition of PEO. No change of gelation time was observed with the addition of $K^+$. Upon gelation, a random coil structure of the silk fibroin was transformed into β-sheet structure. Hydrogels with fibroin concentrations >4 weight percent exhibited network and sponge-like structures based on scanning electron microscopy. Pore sizes of the freeze-dried hydrogels were smaller as the silk fibroin concentration or gelation temperature were increased. Freeze-dried hydrogels formed in the presence of $Ca^{2+}$ exhibited larger pores as the concentration of this ion was increased. Mechanical compressive strength and modulus of the hydrogels increased with increase in protein concentration and gelation temperature.

Methods

Preparation of Silk Fibroin Aqueous Solution

Cocoons of *Bombyx mori*, kindly provided by M. Tsukada (Institute of Sericulture, Tsukuba, Japan) and M. Goldsmith (U. Rhode Island), were boiled for 20 min in an aqueous solution of 0.02M $Na_2CO_3$, and then rinsed thoroughly with distilled water to extract the glue-like sericin proteins and wax. The extracted silk fibroin was then dissolved in 9.3M LiBr solution at 60° C. for 4 hrs, yielding a 20 w/v % solution. This solution was dialyzed in distilled water using a Slide-a-Lyzer dialysis cassette (MWCO 3500, Pierce) for 2 days. The final concentration of silk fibroin aqueous solution was ca. 8 wt %, which was determined by weighing the remaining solid after drying. Silk fibroin film prepared from 8 wt % solutions was evaluated to verify the removal of $Li^+$ ion by XPS; no residual $Li^+$ ion was detected.

Preparation of Concentrated Silk Fibroin Solution by Osmotic Stress

Silk fibroin aqueous solution (8 wt %, 10 ml) was dialyzed against 10~25 wt % polyethylene glycol (PEG, 10,000 g/mol) solution at room temperature by using Slide-a-Lyzer dialysis cassettes (MWCO 3500). The volume ratio of PEG to silk fibroin solution was 100:1. By osmotic stress, water molecules in the silk fibroin solution moved into PEG solution through the dialysis membrane (Parsegian.; V. A., et al., *Methods in Enzymology*, Packer, L., Ed.; Academic Press: 1986; Vol. 127, p 400). After the required time, concentrated silk fibroin solution was slowly collected by syringe to avoid excessive shearing and the concentration was determined. Silk fibroin aqueous solutions with concentration less than 8 wt % were prepared by diluting 8 wt % solutions with distilled water. All solutions were stored at 7° C. before use.

Sol-Gel Transitions

A 0.5 ml of silk fibroin aqueous solution was placed in 2.5 ml flat-bottomed vials (diameter: 10 mm). The vials were sealed and kept at room temperature, 37° C. and 60° C. Gelation time was determined when the sample had developed an opaque white color and did not fall from an inverted vial within 30 sec. To investigate the effect of ions and ion concentration on the process, $CaCl_2$ or KCl solutions were added into the silk fibroin aqueous solution to generate a final salt concentration of 2.5 to 30 mM. The pH of the silk fibroin solution was adjusted with HCl or NaOH solution. For the preparation of silk fibroin-poly(ethylene) oxide (PEO, 900,000 g/mol) solution, the required amount of PEO solution (5 wt %) was added to silk fibroin solution with mild stirring for 5 minutes. The blend ratios of silk fibroin/PEO were 100/0, 95/5, 90/10, 80/20 and 70/30 (w/w).

Wide Angle X-Ray Scattering (WAXS)

X-ray profiles were recorded for freeze-dried silk fibroin solutions and hydrogels using a Brucker D8 X-ray Diffractometer at 40 kV and 20 mA, with Ni-filtered Cu-Kα radiation.

Scanning Electron Microscopy (SEM)

Silk fibroin solutions and hydrogels were frozen at −80° C. and then lyophilized. The samples were fractured in liquid nitrogen and examined using a LEO Gemini 982 Field Emission Gun SEM. To check for artifactual morphological changes due to freeze-drying, an alternative preparation used Karnovsky's fixative at room temperature for 4 hrs. Hydrogels with and without fixative treatment showed little morphological change upon freeze-drying. Pore size was obtained by using ImageJ software developed at the US National Institutes of Health.

Mechanical Properties

Compression tests of hydrogels were performed on an Instron 8511 equipped with a 2.5 kN load cell at room temperature. A crosshead speed was 10 mm/min. The cross-section of samples was 12 mm in diameter and 5 mm in height. The compression test was achieved conventionally as an open-sided method. The compression limit was 98% strain to protect the load cell. Five samples were evaluated for each composition.

Results

Concentrated Silk Fibroin Solutions

Figure 6:
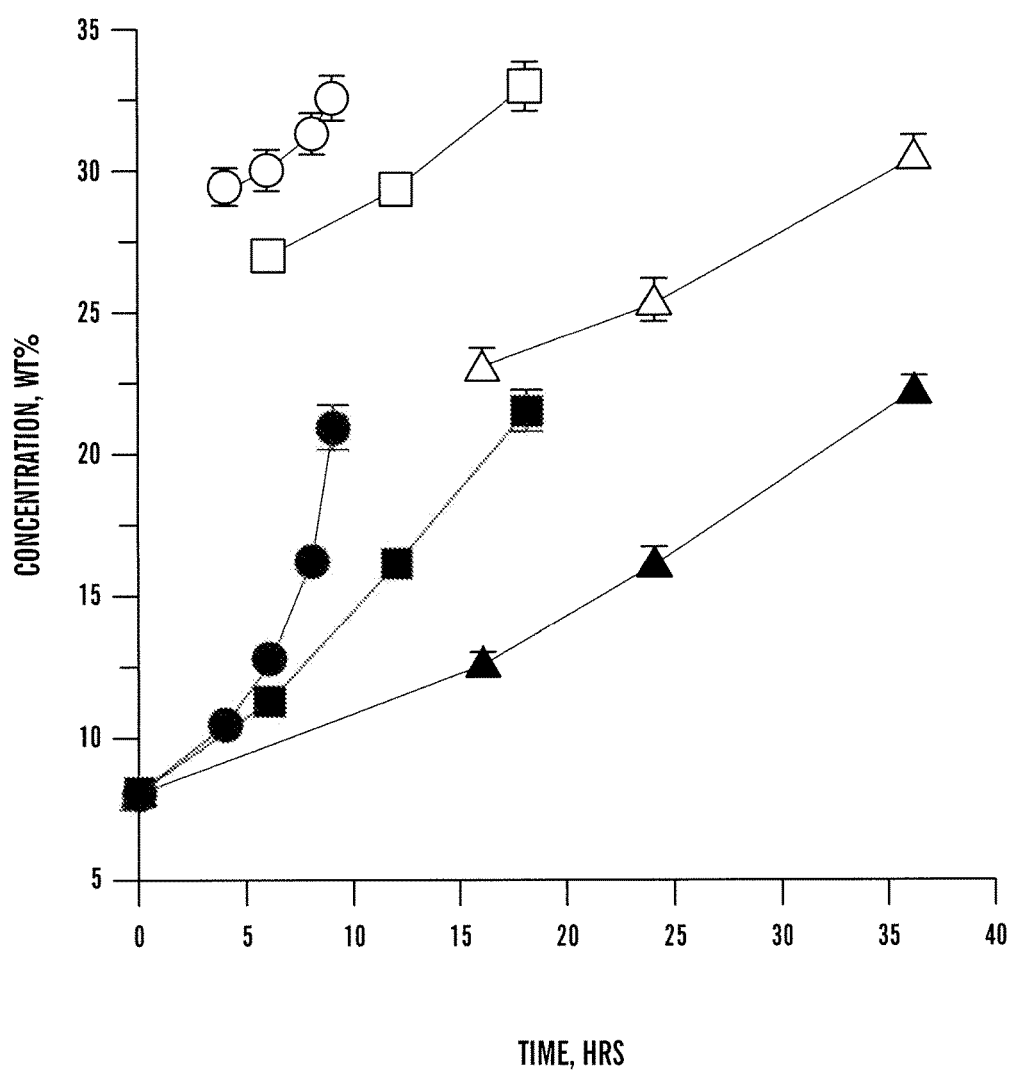
FIG. 6 shows the concentration of silk fibroin solution (filled symbol) and gel (open symbol) prepared by dialysis against PEG solutions (circle; 25 wt %, rectangle; 15 wt %, triangle; 10 wt %) at room temperature. Values are average±standard derivation of 3 samples.

Silk fibroin aqueous solution with an initial concentration of 8 wt % was dialyzed against 10~25 wt % PEG solution at room temperature. Silk fibroin aqueous solution was concentrated over time by osmotic stress and concentrations of ca. 21 wt % were obtained after 9 hrs dialysis against 25 wt % PEG solution (FIG. 6). Longer dialysis times were required to generate higher concentrations of silk fibroin aqueous solution, when lower concentrations of PEG solutions were used. Silk fibroin gels, 23~33 wt %, were spontaneously generated in the dialysis cassettes during the concentration process. These gels were transparent even after drying at room temperature and at 60° C.

Gelation of Silk Fibroin Aqueous Solution

Figure 7:
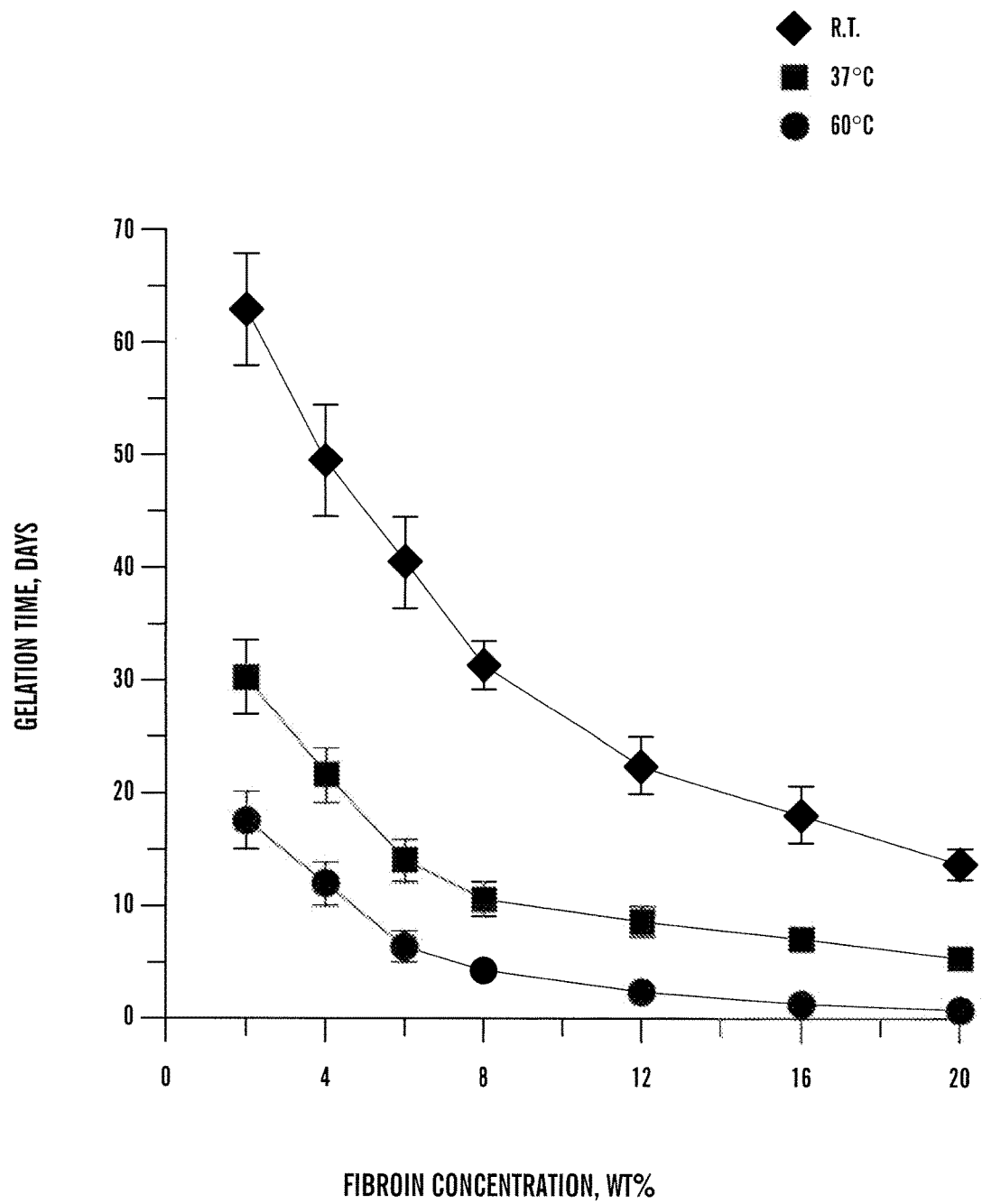
FIG. 7 shows the gelation time of silk fibroin aqueous solutions at various temperatures (pH 6.5~6.8, without ions). Values are average±standard derivation of 7 samples.
Figures 8A, 8B, 8C:
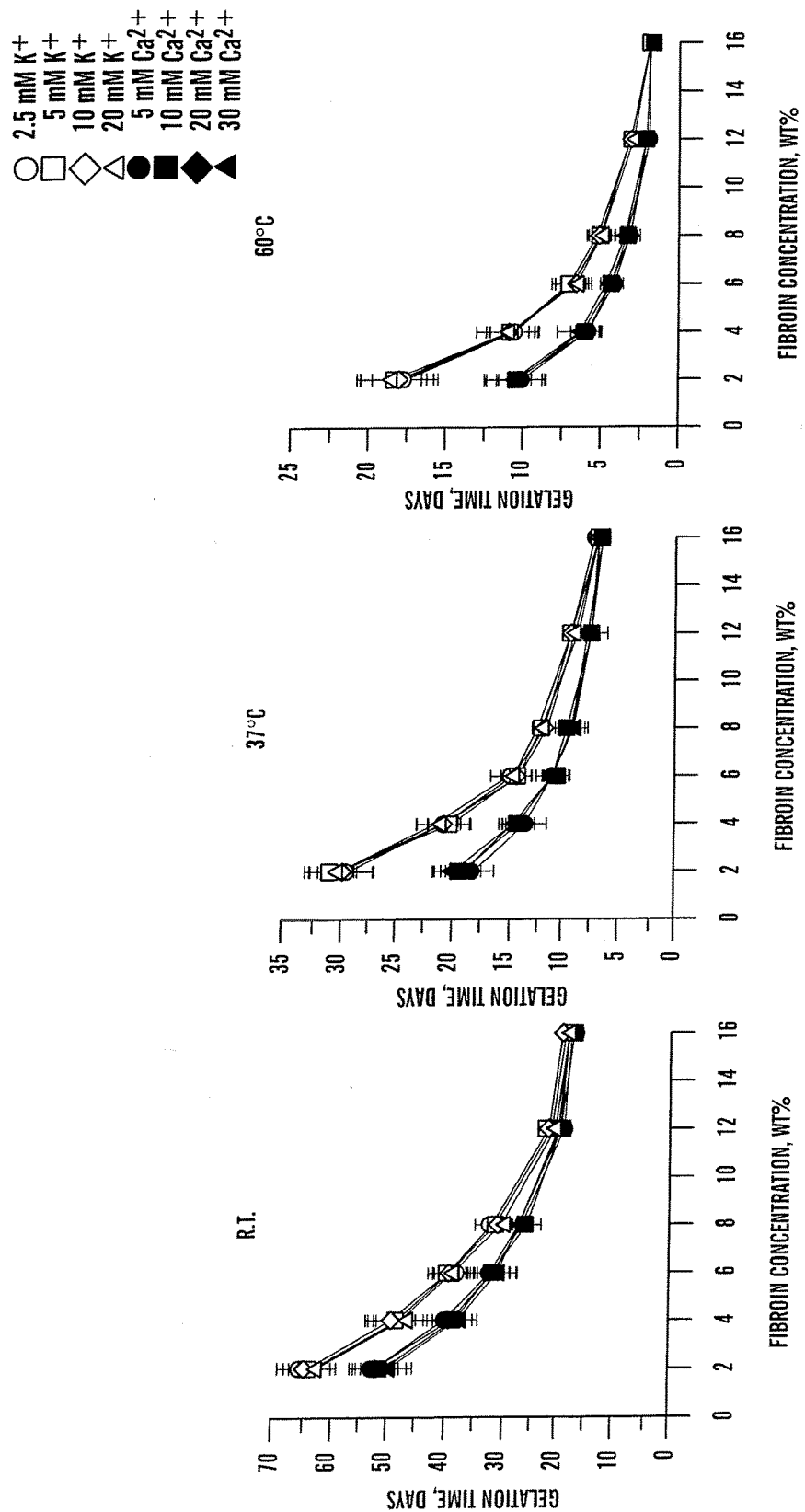
FIGS. 8a, 8b, and 8c show the gelation time of silk fibroin aqueous solutions with different $Ca^{2+}$ (pH 5.6~5.9) and $K^+$ (pH 6.2~6.4) concentrations at (FIG. 8a) room temperature, (FIG. 8b) 37° C.
Figure 9:
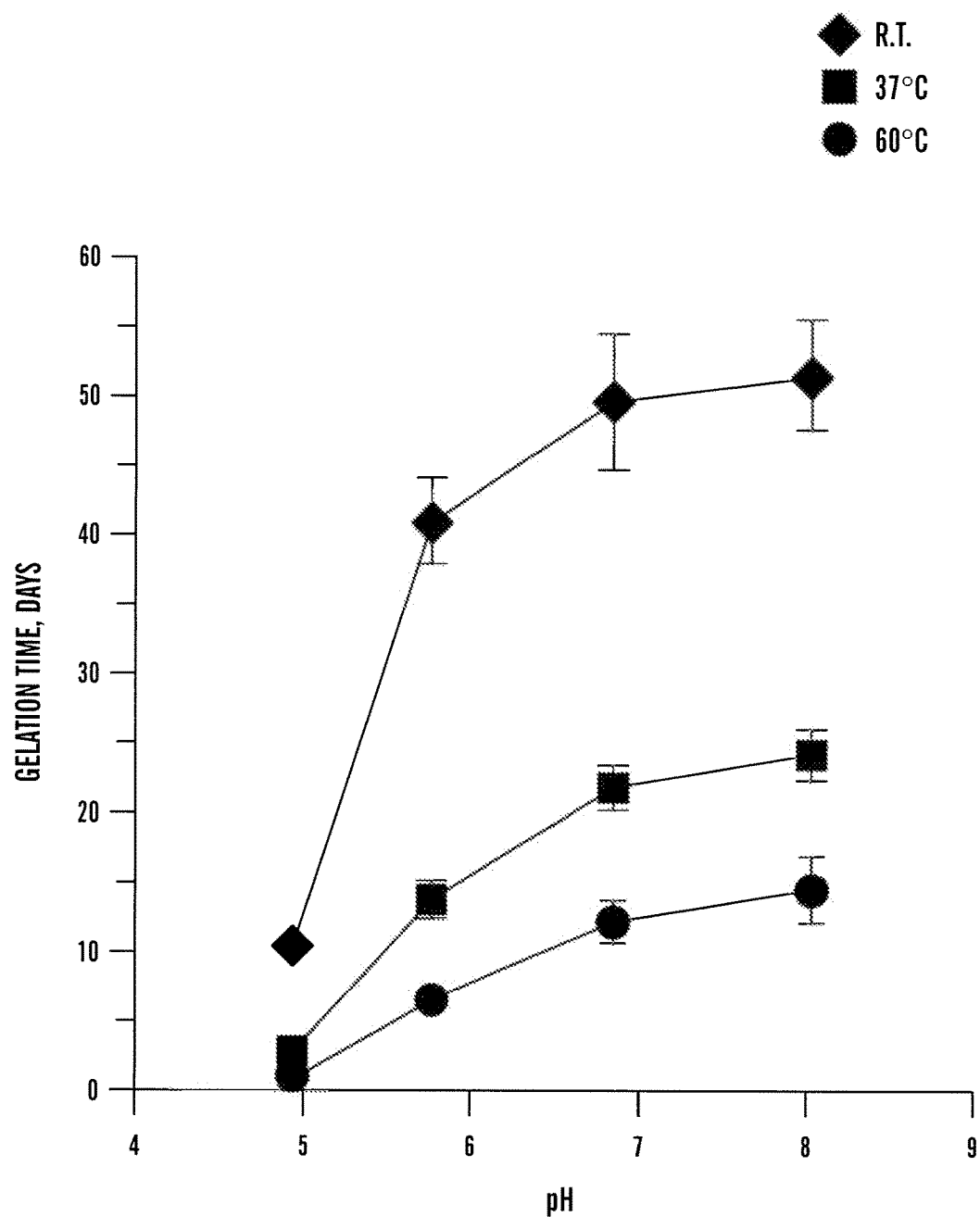
FIG. 9 shows the gelation time of silk fibroin aqueous solutions at various pHs (4 wt % silk fibroin; without ions; room temperature). Values are average±standard derivation of 7 samples.
Figure 10:
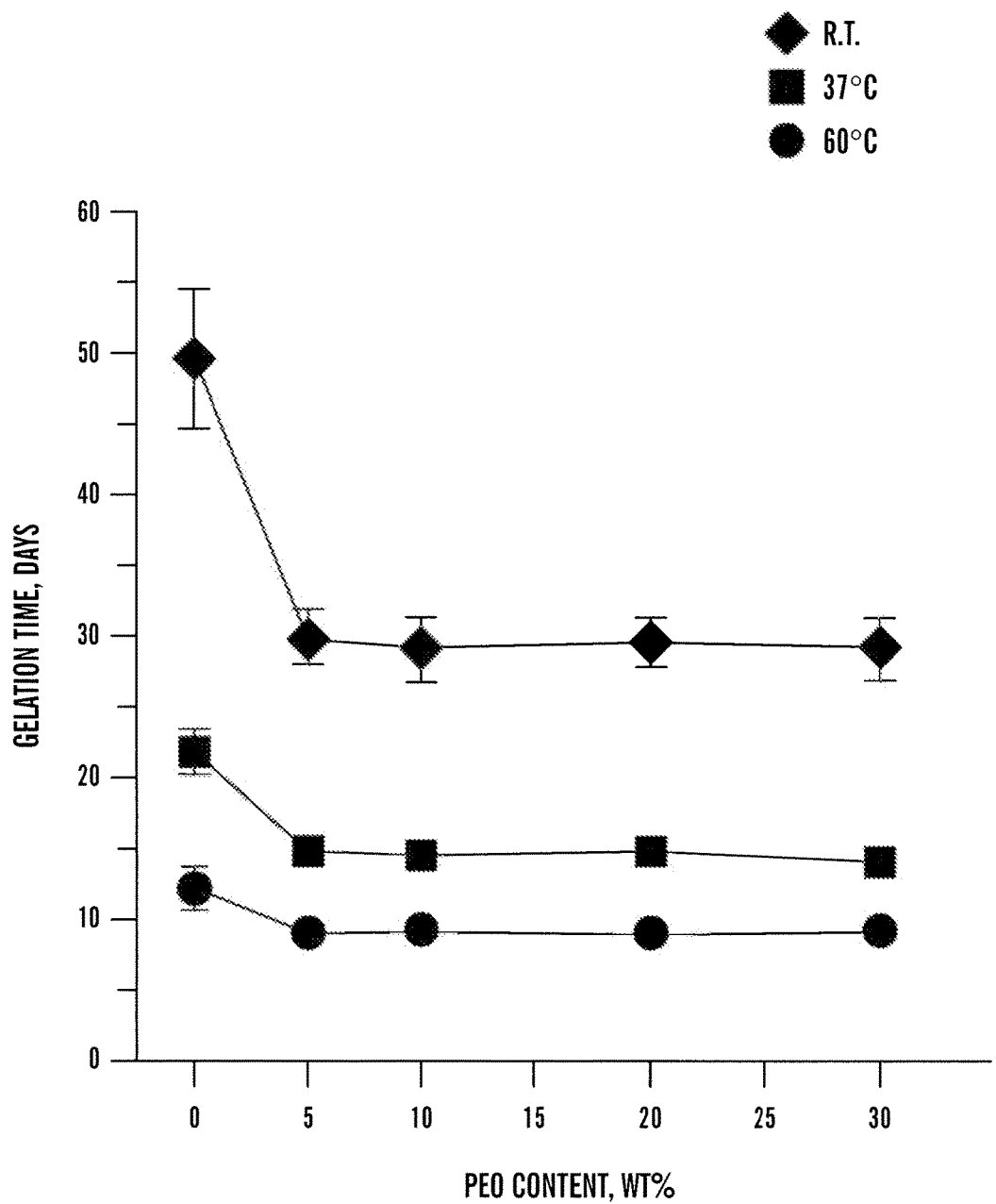
FIG. 10 shows the gelation time of silk fibroin aqueous solutions at various PEO contents (4 wt % silk fibroin; pH 6.1~6.4; without ions; room temperature). Values are average±standard derivation of 7 samples.

The influence of temperature, $Ca^{2+}$ and $K^+$ concentrations, pH and PEO concentration was investigated on the gelation of silk fibroin aqueous solutions. FIG. 7 illustrates the gelation time of silk fibroin aqueous solution (pH 6.5~6.8) at various temperatures. The gelation time of silk fibroin aqueous solution decreased with increase in fibroin content and temperature. Concurrently, a conformational change from random coil to β-sheet structure was observed and the formation of β-sheet structure in the hydrogels was confirmed by X-ray diffraction as described later. FIGS. 8A, 8B, and 8C shows the gelation time of silk fibroin aqueous solution with different $Ca^{2+}$ and $K^+$ concentrations. The pHs of silk fibroin solutions with $Ca^{2+}$ and $K^+$ ions were 5.6~5.9 and 6.2~6.4, respectively. $Ca^{2+}$ resulted in shorter gelation times, whereas there was no change in gelation time with the addition of $K^+$ at any temperature. These results with regenerated silkworm fibroin differ from prior studies in which $K^+$ ions added to solutions of spider silk influenced aggregation and precipitation of the protein, whereas there was no rheological change after addition of $Ca^{2+}$ ions. FIG. 9 shows the gelation time of silk fibroin aqueous solution (4 wt %) at different pHs. Gelation time decreased significantly with a decrease in pH. This behavior is similar to that observed for the silk from the spider, *Araneus diadematus*, which gels at pH 5.5, but behaves as a viscous liquid at pH 7.4 (Vollrath, F., et al., *Proc. R. Soc. London B*, 1998, 265, 817-820); FIG. 10 shows the gelation time of silk fibroin aqueous solution (4 wt %) with different polyethylene oxide (PEO) contents. By adding PEO solution, the pH decreased slightly to the range 6.1~6.4. The gelation time was significantly reduced with the addition of only 5% PEO, whereas there was no difference in gelation time when the concentration was above 5%.

Structural Analysis of Hydrogels

Figure 11B:
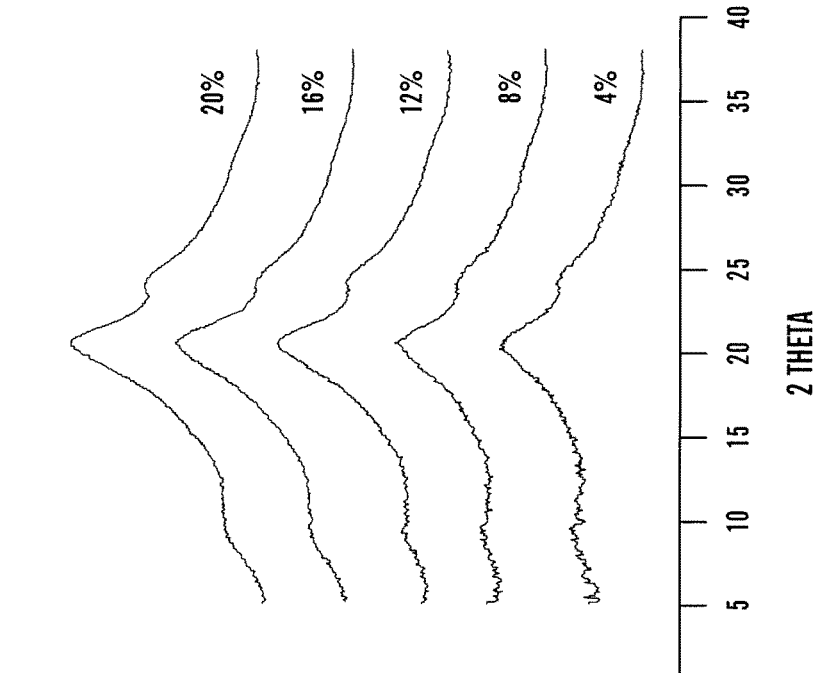
FIGS. 11a and 11b show the X-ray profiles of (FIG. 11a) freeze-dried silk fibroin solutions and (FIG. 11b) hydrogels prepared from silk fibroin aqueous solution at 60° C.
Figure 11A:
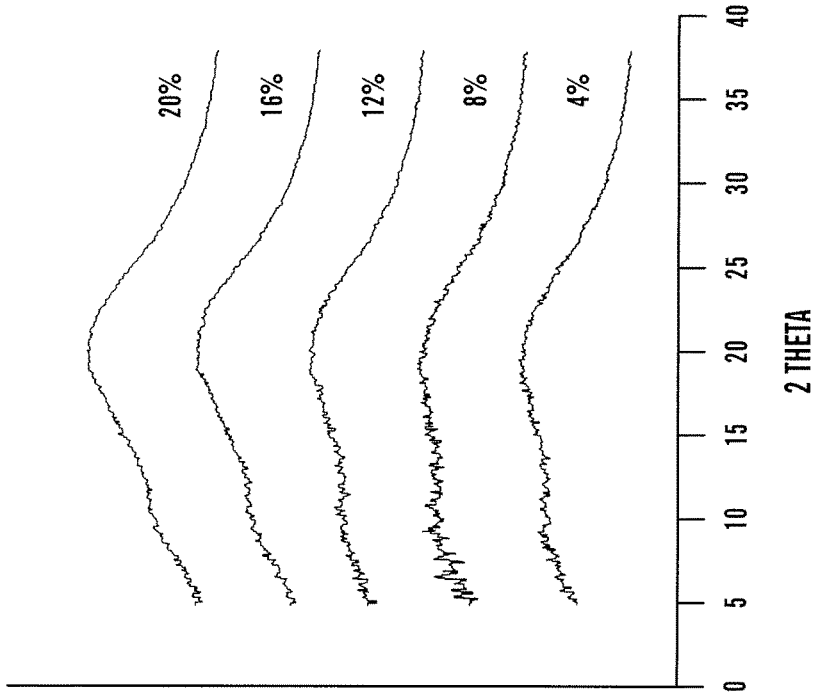

Structural changes in the silk fibroin were determined by X-ray diffraction. FIG. 11 shows X-ray profiles of freeze-dried silk fibroin solutions and hydrogels prepared from silk fibroin aqueous solutions. When silk fibroin solutions were frozen at low temperature, below the glass transition (−34~−20° C.), the structure was not significantly changed (Li, M., et al., *J. Appl. Polym. Sci.* 2001, 79, 2185-2191). The freeze-dried silk fibroin samples exhibited a broad peak at around 20° regardless of the silk fibroin concentration, indicating an amorphous structure. Silk fibroin in aqueous solution at neutral pH exhibited a random coil conformation. (Magoshi, J., et al., *Polymeric Materials Encyclopedia*; Salamone, J. C., Ed.; CRC Press: NewYork, 1996; Vol. 1, p. 667; Magoshi, J., et al., *Polymeric Materials Encyclopedia*; Salamone, J. C., Ed.; CRC Press: NewYork, 1996; Vol. 1, p. 667). All hydrogels prepared from silk fibroin solutions showed a distinct peak at 20.6° and two minor peaks at around 9° and 24°. These peaks were almost the same as those of the β-sheet crystalline structure of silk fibroin. (Ayub, Z. H., et al., *Biosci. Biotech. Biochem.* 1993, 57, 1910-1912; Asakura, T., et al., *Macromolecules* 1985, 18, 1841-1845). These peaks indicate β-crystalline spacing distances of 9.7, 4.3 and 3.7 Å according to 9°, 20.6° and 24°, respectively. From the results of X-ray diffraction, the gelation of silk fibroin solutions induced a conformational transition from random coil to β-sheet as previously reported. (Ayub, Z. H., et al., *Biosci. Biotech. Biochem.* 1993, 57, 1910-1912; Hanawa, T., et al., *Chem. Pharm. Bull.* 1995, 43, 284-288; Kang, G. D., et al., *Marcromol. Rapid Commun.* 2000, 21, 788-.791).

Morphology of Freeze-Dried Hydrogels

Morphological features of silk fibroin solutions and hydrogels were observed by SEM after freeze-drying at −80° C. Freeze-dried silk fibroin solutions of 4~12 wt % showed leaf-like morphologies. Freeze-dried silk fibroin solutions of 16 wt % and 20 wt % exhibited network and sponge-like structures with pore sizes of 5.0±4.2 µm and 4.7±4.0 µm, respectively. By SEM imagery it was determined that freeze-dried hydrogels prepared from 4 wt % silk fibroin solution showed leaf-like morphologies and interconnected pores regardless of temperature and at higher fibroin concentrations than 4 wt % sponge-like structures were observed. The pore sizes of freeze-dried hydrogels (<1.1±0.8 µm) were smaller than those observed for the freeze-dried silk fibroin solution samples. Pore sizes in the freeze-dried hydrogels decreased with increase in silk fibroin concentration, and pore sizes decreased as temperature increased at the same silk fibroin concentration. The 4 wt % freeze-dried hydrogels with $Ca^{2+}$ ions showed network and sponge-like structures, whereas the 4 wt % freeze-dried hydrogels with $K^+$ ions had a leaf-like morphology. In freeze-dried hydrogels with fibroin concentrations >4 wt %, pore sizes of freeze-dried hydrogels with $Ca^{2+}$ were larger than those of freeze-dried hydrogels prepared from silk fibroin aqueous solutions without $Ca^{2+}$ ions. Interestingly, pore size was larger in freeze-dried hydrogels with the same silk fibroin concentration with an increase in $Ca^{2+}$ concentrations. In contrast to freeze-dried hydrogels with $Ca^{2+}$, pore sizes of freeze-dried hydrogels with $K^+$ showed sizes similar to those of freeze-dried hydrogels prepared from silk fibroin aqueous solutions. These results imply that $Ca^{2+}$ was more effective in inducing interactions among the silk fibroin chains than the $K^+$. This result is also consistent with the earlier data wherein $Ca^{2+}$ resulted in shorter gelation times than K.

Mechanical Properties of Hydrogels

Figures 12A, 12B, 12C:
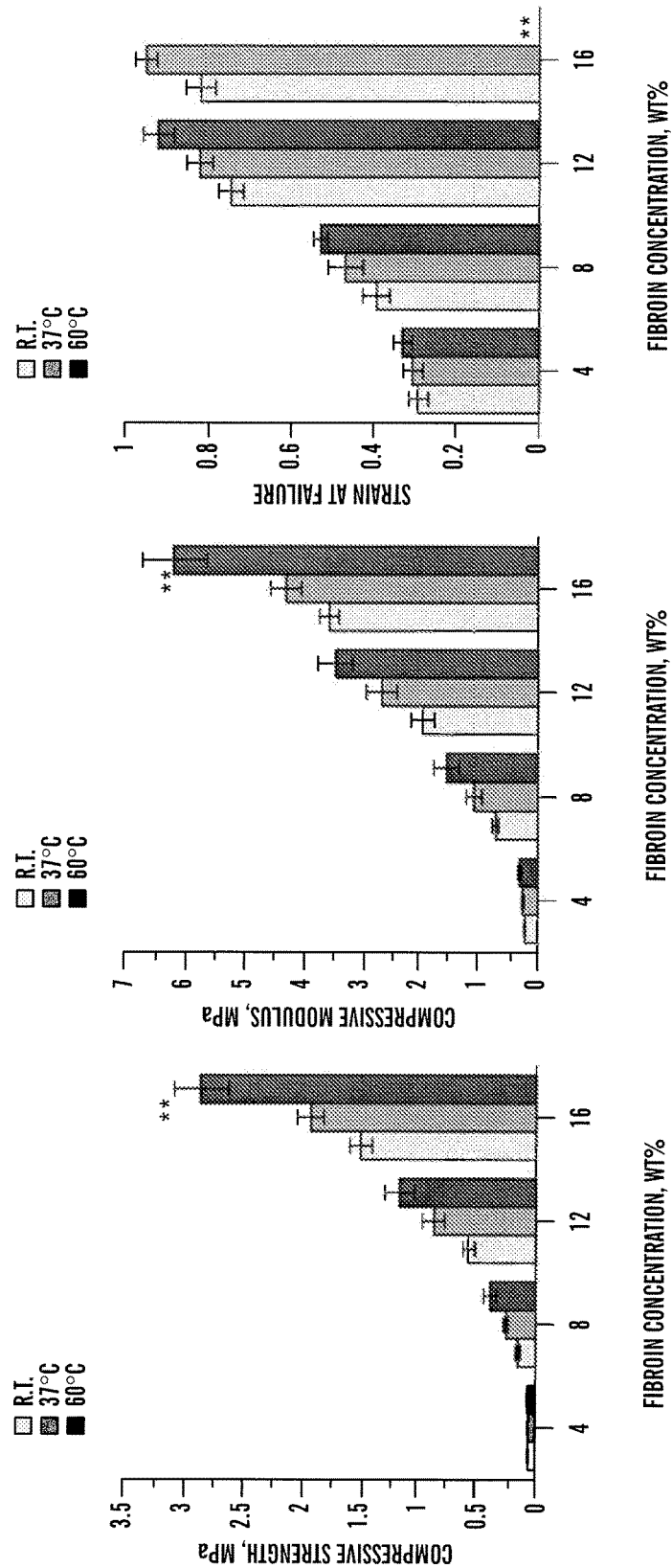
FIGS. 12a, 12b, and 12c show the compressive strength (FIG. 12a), compressive modulus (FIG. 12b) and strain at failure (FIG. 12c) of hydrogels prepared from silk fibroin aqueous solutions at various temperatures. **: Hydrogel prepared at 60° C. with the silk fibroin concentration of 16 wt % was not crushed under the conditions used in the study. Values are average±standard derivation of 5 samples.

The compressive strength and modulus of hydrogels prepared from silk fibroin aqueous solutions increased with an increase in silk fibroin concentration (FIGS. 12a and 12b). The improvement in mechanical properties was attributed to the increase in polymer concentration accompanied with the decrease in pore size. At the same silk fibroin concentration, hydrogels prepared at higher temperature showed higher compressive strengths and moduli due to the decreased pore size. Hydrogels with 4~8 wt % fibroin showed less than 55% strain, while hydrogels with 12~16 wt % fibroin revealed larger strains ranging from 75% to 96% (FIG. 12c). The effect of pore size was considered since the smaller pore size distributes stress in the hydrogel more evenly to resist stress concentration. The smaller pore size and increased number of pores also function as a barrier against crack propagation.

Discussion

Gelation occurs due to the formation of inter- and intramolecular interactions among the protein chains, including hydrophobic interactions and hydrogen bonds (Ayub, Z. H., et al., *Biosci. Biotech. Biochem.* 1993, 57, 1910-1912; Hanawa, T., et al., *Chem. Pharm. Bull.* 1995, 43, 284-288; Kang, G. D., et al., *Marcromol. Rapid Commun.* 2000, 21, 788-.791). With an increase in fibroin content and temperature, interactions among the fibroin chains increases. Silk fibroin molecules are thereby able to interact more readily, leading to physical crosslinks.

The concentration of $Ca^{2+}$ ion in the silkworm (*Bombyx mori*) increases from 5 mM to 15 mM as silk progresses toward the spinneret, while $K^+$ ion is present at 5~8 mM.[3] Several calcium salts are known to dissolve silk fibroin because of strong interactions with the fibroin (Ajisawa, A. *J. Seric. Sci. Jpn.* 1998, 67, 91-94; Ha, S. W., et al., *Biomacromolecules* 2003, 4, 488-496). Rheological measurements of dilute solutions of silk fibroin from *Bombyx mori* revealed that the protein chains tend to form clusters by ionic interaction between $COO^-$ ions of amino acid side chains in the fibroin and divalent ions such as $Ca^{2+}$ or $Mg^{2+}$ (Ochi, A., et al., *Biomacromolecules* 2002, 3, 1187-1196). Through these interactions, the pH of silk fibroin solutions with $Ca^{2+}$ ions was significantly lower than that of silk fibroin solutions in the absence of these ions, whereas the addition of monovalent ions such as $K^+$ showed only a slight decrease of pH. With lower pH, repulsion among silk fibroin molecules decreases and interactions among the chains is easier, resulting in stronger potential for the formation of β-sheet structure through hydrophobic interactions. A pH near the isoelectric point (pI=3.8-3.9) (Ayub, Z. H., et al., *Biosci. Biotech. Biochem.* 1993, 57, 1910-1912; Kang, G. D., et al., *Marcromol. Rapid Commun.* 2000, 21, 788-791) of silk fibroin accelerated the sol-gel transition of silk fibroin aqueous solutions in a fashion similar to other proteins that aggregate near their isoelectric points.

These outcomes may reflect subtle differences in how different silk proteins from different organisms utilize physiologically relevant ions to facilitate sol-gel transitions. Divalent ions may induce aggregation of silk fibroin molecules by ionic interactions with negatively charged amino acids present particularly near the chain ends of the heavy chain fibroin. The lack of response to different concentrations of $Ca^{2+}$ may suggest a broad window of response physiologically or perhaps a role for combinations of ions to fully control this process in vivo or in vitro. Additional studies will be required to elucidate these relationships, particularly when considered in concert with observations on domain mapping of silks related to processing environments (Bini, E., et al., *J. Mol. Biol.* 2004, 335, 27-40).

The movement of water from the silk fibroin molecules to the hydrophilic PEO facilitates inter- and intramolecular interactions among the protein molecules and the subsequent formation of the β-sheet structure. This transition is evident with silk based on our recent mechanistic understanding of the process (Jin, H. J., et al., *Nature* 2003, 424, 1057-1061). These transitions can be induced by direct addition of PEO into the fibroin aqueous solutions, or via separation from the aqueous solutions across a dialysis membrane (with PEG). Thus, direct contact between the protein and the PEO is not required, only the facilitation of water transport from the protein to the PEO/PEG to drive the sol-gel transition.

Conclusions

From the primary sequence, silkworm silk fibroin heavy chain is composed of seven internal hydrophobic blocks and seven much smaller internal hydrophilic blocks, with two large hydrophilic blocks at the chain ends (Zhou, C. Z., et al., *Nucleic Acids Res.* 2000, 28, 2413-2419; Jin, H. J., et al., *Nature* 2003, 424, 1057-1061). The percentage of hydrophobic residues in silk fibroin is 79% (Braun, F. N., et al., *Int. J. Biol. Macromol.* 2003, 32, 59-65) and the repetitive sequence in hydrophobic residues consists of GAGAGS peptides that dominate the β-sheet structure forming crystalline regions in silk fibroin fibers and films (Mita, K., et al., *J. Mol. Evol.* 1994, 38, 583-592). The formation of these β-sheets results in insolubility in water (Valluzzi, R., et al., *J. Phys. Chem. B* 1999, 103, 11382-11392). Hydrophobic regions of silk fibroin in aqueous solution assemble physically by hydrophobic interactions and eventually organize into hydrogels (Jin, H. J., et al., *Nature* 2003, 424, 1057-1061). Silk fibroin concentration, temperature, $Ca^{2+}$, pH and PEO affected the gelation of the silk fibroin aqueous solutions. With increase in fibroin content and temperature, physical crosslinking among silk fibroin molecules formed more easily. $Ca^{2+}$ ions accelerated these interactions, presumably through the hydrophilic blocks at the chain ends. The decrease in pH and the addition of a hydrophilic polymer decreased repulsion between silk fibroin molecules and promoted the desorption of water from the protein, resulting in shorter gelation times. Upon gelling, a conformational transition from random coil to β-sheet structure was induced and promoted the insolubility and stability of silk fibroin hydrogels in water. Silk fibroin hydrogels had network and sponge-like structures. Pore size was smaller with increased silk fibroin concentration and gelation temperature. Freeze-dried hydrogels showed larger pore sizes with increases in $Ca^{2+}$ concentrations than freeze-dried hydrogels prepared from silk fibroin aqueous solutions at the same fibroin content. The compressive strength and modulus of hydrogels prepared from silk fibroin aqueous solution without ions increased with increase in protein concentration and gelation temperature.

Hydrogels from natural polymers, such as collagen, hyaluronate, fibrin, alginate and chotosan, have found numerous applications in tissue engineering as well as in drug delivery. However, they generally offer a limited range of mechanical properties (Lee, K. Y., et al., *Chem. Rev.* 2001, 101, 1869-1879). In contrast, silk fibroin provides an important set of material options in the fields of controlled release, biomaterials and scaffolds for tissue engineering because of combination with impressive mechanical properties, biocompatibility, biodegradability and cell interaction (Altman, G. H., et al., *Biomaterials* 2003, 24, 401-416; Cappello, J., et al., *J. Control. Release* 1998, 53, 105-117; Foo, C. W. P., et al., *Adv. Drug Deliver. Rev.* 2002, 54, 1131-1143; Dinerman, A. A., et al., *J. Control. Release* 2002, 82, 277-287; Megeed, Z., et al., *Adv. Drug Deliver. Rev.* 2002, 54, 1075-1091; Petrini, P., et al., *J. Mater. Sci-Mater. M* 2001, 12, 849-853; Altman, G. H., et al., *Biomaterials* 2002, 23, 4131-4141; Panilaitis, B., et al., *Biomaterials* 2003, 24, 3079-3085).

Example IV

Bone Regeneration Using Three-Dimensional Aqueous-Derived Silk Scaffolds

We have examined the bone regeneration of human bon marrow stem cells on three-dimensional silk scaffolds from aqueous silk solutions of the invention. To study the ability of the silk scaffolds to support the growth and differentiation of the bone marrow stem cells, we have used the silk scaffolds without any decoration.
Methods
Materials Bovine serum, Dulbecco's Modified Eagle Medium (DMEM), Minimal essential medium-α modification (αMEM), basic Fibroblast growth factor (bFGF), Penicillin-Streptomycin (Pen-Strep), Fungizone, non essential amino acids, trypsin were from Gibco (Carlsbad, Calif.). Ascorbic acid phosphate, Histopaque-1077, dexamethasone, and β-glycerolphosphate were from Sigma (St. Lois, Mo.). All other substances were of analytical or pharmaceutical grade and obtained from Sigma. Silkworm cocoons were kindly supplied by M. Tsukada (Institute of Sericulture, Tsukuba, Japan) and Marion Goldsmith (University of Rhode Island, Cranston, R.I.).
Preparation of Scaffolds Aqueous-derived silk scaffolds were prepared by adding 4 g of granular NaCl (particle size; 1000~1180 μm) into 2 ml of 8 wt % silk fibroin solution in disk-shaped Teflon containers. The container was covered and left at room temperature. After 24 hrs, the container was immersed in water and the NaCl was extracted for 2 days. HFIP-derived silk scaffolds were prepared by adding 4 g of granular NaCl (particle size; 850~100 μm) into 2 ml of 8 wt % silk fibroin in HFIP. The containers were covered to reduce of HFIP and to provide the sufficient time for more homogeneous distribution of the solution. The solvent was evaporated at room temperature for 3 days. After the composite of silk/porogen was treated in methanol for 30 min to induce β-sheet structure and insolubility in aqueous solution, the composite was immersed in water to remove NaCl for 2 days. The porous silk scaffolds were air-dried.
Human Bone Marrow Stem Cell Isolation and Expansion Total bone marrow (25 cm$^3$, Clonetics, Santa Rosa, Calif.) was diluted in 100 ml of isolation medium (5% FBS in RPMI 1640 medium). Cells were separated by density gradient centrifugation. Briefly, 20 ml aliquots of bone marrow suspension were overlaid onto a poly-sucrose gradient (1,077 g/cm$^3$, Histopaque, Sigma, St. Louis, Mo.) and centrifuged at 800×g for 30 min at room temperature. The cell layer was carefully removed, washed in 10 ml isolation media, pelleted and contaminating red blood cells were lysed in 5 ml of Pure-Gene Lysis solution. Cells were pelleted and suspended in expansion medium (DMEM, 10% FBS, 1 ng/ml bFGF, 100 U/ml penicillin, 100 μg/ml streptomycin, 0.25 μg/ml fungizone, nonessential amino acid) and seeded in 75 cm$^2$ flasks at a density of 5×104 cells/cm$^2$. The adherent cells were allowed to reach approximately 80% confluence (12-17 days for the first passage). Cells were trypsinized, replated and passage 2 (P2) cells (80% confluence after 6-8 days), were used for the experiments.
In Vitro Culture For examination of cell growth and differentiation in vitro on silk scaffolds, BMSC (5×10$^5$ cells/scaffold, passage 2) was seeded onto prewetted (α-MEM, overnight) silk scaffolds. After 24 h, the medium was removed and cultures were maintained in individual wells of 6-well plates. Osteogenic media were α-MEM supplemented with 10% FBS, nonessential amino acid, 50 μg/ml ascorbic acid-2-phosphate, 10 nM dexamethasone, and 7 mM β-glycerolphosphate in the presence of penicillin and streptomycin and fungizone. Cultures were maintained at 37° C. in a humidified incubator supplemented with 5% CO$_2$. Half of the medium was changed every 2-3 days.
Biochemical Analysis and Histology Scaffolds were cultured for 2 and 4 weeks in osteogenic media and processed for biochemical analysis and histology. For DNA analysis, 3-4 scaffolds per group and time point were disintegrated. DNA content (n=3-4) was measured using the PicoGreen assay (Molecular Probes, Eugene, Oreg.), according to the protocol of the manufacturer. Samples were measured flurometrically at an excitation wavelength of 480 nm and an emission wavelength of 528 nm. For total calcium content, samples (n=4) were extracted twice with 0.5 ml 5% trichloroacetic acid. Calcium content was determined by a colorimetric assay using o-cresolphthalein complexone (Sigma, St. Louis, Mo.). The calcium complex was measured spectrophotometrically at 575 nm. Alkaline phosphatase activity was measured using a biochemical assay from Sigma (St. Louis, Mo.), based on conversion of p-nitrophenyl phosphate to p-nitrophenol, which was measured spectrophotometrically at 405 nm.
RNA Isolation, Real-Time-Reverse Transcription Polymerase Chain Reaction (Real Time RT-PCR)

Fresh scaffolds (n=3-4 per group) were transferred into 2 ml plastic tubes and 1.0 ml Trizol was added. Scaffolds were disintegrated using steel balls and a Microbeater. Tubes were centrifuged at 12000 g for 10 minutes and the supernatant was transferred to a new tube. Chloroform (200 μl) was added to the solution and incubated for 5 minutes at room temperature. Tubes were again centrifuged at 12000 g for 15 minutes and the upper aqueous phase was transferred to a new tube. One volume of 70% ethanol (v/v) was added and applied to an RNeasy mini spin column (Quiagen, Hilden, Germany). The RNA was washed and eluted according to the manufacturer's protocol. The RNA samples were reverse transcribed into cDNA using oligo (dT)-selection according to the manufacturer's protocol (Superscript Preamplification System, Life Technologies, Gaithersburg, Md.). Collagen type I, Collagen type II, Alkaline phosphatase, bone sialoprotein and Osteopontin gene expression were quantified using the ABI Prism 7000 Real Time PCR system (Applied Biosystems, Foster City, Calif.). PCR reaction conditions were 2 min at 50° C., 10 min at 95° C., and then 50 cycles at 95° C. for 15 s, and 1 min at 60° C. The expression data were normalized to the expression of the housekeeping gene, glyceraldehyde-3-phosphate-dehydrogenase (GAPDH). The GAPDH probe was labelled at the 5' end with fluorescent dye VIC and with the quencher dye TAMRA at the 3' end. Primer sequences for the human GAPDH gene were: Forward primer 5'-ATG GGG AAG GTG AAG GTC G-3' (SEG ID NO: 1), reverse primer 5'-TAA AAG CCC TGG TGA CC-3' (SEQ ID NO: 2), probe 5'-CGC CCA ATA CGA CCA AAT CCG TTG AC-3'(SEQ ID NO: 3). Primers and probes for alkaline phosphatase, bone sialoprotein (BSP), osteopontin and were purchased from Applied Biosciences (Assay on Demand #, Hs 00240993 ml (ALP), Hs 00173720 ml (BSP), Hs 00167093 ml (osteopontin)).

Western Blotting Analysis

For total protein extraction, cells were lysed in RIPA buffer [50 mM Tris-HCl, pH 8.0, 150 mM NaCl, 1% Nonidet P-40 (NP-40), 0.2% SDS, 5 mM NaF] containing protease inhibitors and phosphatase inhibitors. Protein content was measured by the Bradfod method. Proteins were resolved by 3-8% SDS-PAGE and transferred to membranes. Blots were probed with the primary antibody for 12 h at 4° C., washed, and incubated with the appropriate peroxidases labed secondary antibodies for 1 h at room temperature. Protein bands were revealed by ECL (Armersham-Pharmacia,)

Scanning Electron Microscopy (SEM) Analysis

The polymeric surfaces prior to and after cell attachment were examined by scanning electron microscopy (SEM). Matrices were fixed using Karnovsky's fixative for 24 h, and washed three times in CMPBS to remove residual fixative. The samples were then dried using a graded series of ethanol (50~100%) at 15 min intervals. After drying, the samples were sputter coated with gold and examined with a LEO Gemini 982 Field Emission Gun SEM.

Histological Evaluation

After fixation with 4% phosphate-buffered formaldehyde for at least 24 hours, specimens were embedded within paraffin and sectioned (4 µm). Using standard histochemical techniques, serial sections were stained with hematoxylin and eosin and alcian blue.

Results

SEM Analysis

Characterization of the 3D-silk scaffolds was determined by assessment of structurally by SEM for the analysis of pore size distribution and surface topography. SEM analysis showed the water-silk scaffold had the interconnected porous networks with an average pore size 920±50 µm. Pore surfaces had an appearance of a rough structure with non-homogenous micropores. However, HFIP-silk scaffold had the poor interconnected porous networks with an average pore size 900±40 µm and showed the smooth surface structure. BMSCs (passage 2) were seeded in water-silk sponge and HFIP-silk sponge. More cells adhered to the water-silk sponge than to the HFIP-silk sponge. Water-silk sponge facilitated cell seeding. And BMSCs were homogeneously distributed throughout the water-silk sponge. In contrast, the distribution of BMSCs on HFIP-silk sponge was not homogenous. BMSCs growth was observed on water-silk sponge. SEM confirmed extensive growth of BMSCs on water-silk sponge, followed by growth for up to 4 weeks.

Gross Examination

The cell-scaffold constructs were cultured in osteogenic media under a 5% $CO_2$ atmosphere at 37° C. Constructs were cultured for up to 28 days in 6 well plates. The BMSCs-water-silk constructs were became rounded after culturing but BMSCs-HFIP-silk constructs were originally flat and did not change after culturing. The tissue formed in the water-silk scaffold was whitish, hard to the touch and with surgical forceps. But the BMSCs seeded in the HFIP-silk scaffold did not form whitish tissue. No significant difference was noted 2- and 4-week specimens on gross examination. And homogenous cellular distribution of BMSCs within the water-silk scaffold was qualitatively demonstrated by the uniformity of matrix staining (indicative of MTT conversion by viable cells) on the surface and throughout the center of the scaffold. But HFIP-silk scaffold displayed intense staining along the surface of construct and regions of weak staining within the interior of the construct.

Biochemical Analysis

The porosity of the 3D matrices was ca 92% in both water- and HFIP-silk. The compressive strength and modulus water-silk scaffolds were 100±10 kPa and 1300±40 kPa. Those of HFIP-scaffolds were 50±5 kPa and 210±60 kPa.

The total number of cells cultured on the scaffolds was quantified using a DNA assay over the time course of the study. For water-silk scaffolds seeded with cells suspended in medium, there was an increase from 51,000±12,000 cells after initial seedings to 150,000±12,000 cells after 28 days of culture. HFIP-silk scaffolds seeded with cells suspended in medium did not show significant proliferation from the 8,000±3,400 cells after the initial cell seeding to 32,000±11,000 cells after 28 days of culture.

Alkaline phosphatase (ALPase) activity, an indicator of the osteoprogenitor cell's commitment to the osteoblastic phenotype, was measured on a per-scaffold. For water-silk scaffold, there was a significant increase in ALPase activity after 28 days in culture (9.7±0.3 mmol/scaffold) compared to 1 day (0.4±0.01 mmol/scaffold). After 28 days of culture for HFIP-silk scaffold, 2.9±0.12 mmol per scaffold was detected.

The total calcium content of each sample was measured on a per-scaffold. Significant calcium deposition (10.5±0.65 µg/scaffold) was found after 28 days of culture in osteogenic media for water-silk scaffold. After 28 days of culture for HFIP-silk scaffold, there was 1.4±0.1 µg of $Ca^{2+}$ per scaffold.

Expression of Osteogenic Differentiation Associated Genes

To characterize the bone-like tissue produced by BMSC, the expression of several osteogenic differentiation and condrogenic differentiation marker genes were quantified using real-time RT-PCR assays. The genes analyzed included the osteogenic differentiation markers collagen type I (Col I), alkaline phosphatase (ALP), osteopontin (OP), bone sialoprotein (BSP), and the condrogenic differentiation marker collagen type II (Col II). The transcription level (normalized to GAPDH within the linear range of amplification) differences between scaffold types were significant. Col I, ALP, and OP transcription levels increased in water-silk scaffold when compared with HFIP-silk scaffold. After 28 days of culture, gene expression of Col I, ALP and BSP was significantly increased by 190%, 1100% and 10500%, respectively, in water-silk scaffolds when compared with after 1 days of culture. However, OP and Col II expression was significantly decreased. BSP expression was regulated similarly in water-silk scaffolds and HFIP-silk scaffolds. The differences between scaffold types were not statistically significant.

Expression of Osteogenic Differentiation Associated Proteins

In 3-D water-silk scaffold culture condition, human bone marrow stem cells expressed the osteoblast markers. In comparison to HFIP-silk constructs, the expression of Col I showed significant increase of protein levels under water-silk culture condition after 2 weeks. However the expression of Col I was decreased after 4 weeks culture under the both conditions. After 28 days of culture, the expression of OP was increased in water-silk constructs. The protein showed two bands, of which that at the highest molecular weight was assumed to be highly glycosilated, sulfated or phosphorylated (Singh et al., *J Biol Chem*, 1990, 65:18696-18701). The other protein of bone, BSP was expressed in cells cultured both in water-silk scaffolds and in HFIP-silk scaffolds. However its expression was increased in HFIP-silk constructs after 28 days of culture.

We also analyzed the expression of matrix metalloproteinase 13 (MMP13) and Col II. MMP13 was expressed in only water-silk constructs. And the Col II was downregulated in both culture conditions after 4 weeks.

Histological Examination

Histological examination of these specimens using hematoxylin and eosin stains revealed that the percentage of osteoblast-like cells in their cuboidal or columnar morphology increased with an increase in the culture period in water-silk constructs. After 14 days of culture, almost all pores were filled with connective tissue, fibroblasts and cuboidal osteoblast-like cells. After 28 days, the pores were filled with extracellular matrix, osteoblast-like cells and few cells with fibroblast-like morphology. However, the histological sections of HFIP-silk scaffolds demonstrated that there was a sparse distribution of cells, with their majority forming a cell layer near the scaffold's surface. After 28 days of culture, the majority of cells within HFIP-silk constructs displayed a flat fibroblastic morphology.

After culture in osteogenic media, extracellular matrices of proteoglycan by alcian blue stains revealed that proteoglycans were detected in water-silk constructs. No proteoglycn was histologically detected in HFIP-silk constructs.

Discussion

The silk protein-based matrix scaffolds are of current interest for bone tissue engineering. These scaffolds exhibit higher mechanical properties than the other common biodegradable synthetic and natural polymers such as PGA-PLA copolymers and collagen. HFIP have been used to prepare porous silk fibroin materials. Although HFIP-silk scaffolds are known for their unique mechanical properties, these natural polymers lack cell-recognition signals, which results in insufficient cell adhesion. To overcome this problem, a number of approaches have been developed, including: surface modification with arginine-glycine-aspartic acid (RGD), and hybrid with naturally derived biodegradable polymers.

Cell adhesion is known as an important cellular process because it directly influences cell growth and differentiation. In the present example, used the silk scaffolds without any modification. We observed sufficient cell adhesion in water-silk scaffolds. More cells adhered to the water-silk scaffolds than to the HFIP-silk scaffolds. Variations in surface texture, or microtopography can affect the cellular response. It was found that a higher percentage of cells attached to the rougher surface. SEM analysis and histological analysis showed our water-silk scaffold had the rough structure with homogenous pores. However, HFIP-silk scaffold had the smooth surface structure.

With respect to the microstructures of the porous scaffolds, high porosity (>90%) and interconnected pore network are desirable. In addition, the preferred pore size is generally in the range of 50-500 μm to permit the ingrowth of cells and regeneration of tissue (Katoh K. et al., Biomaterials 2004, 25: 4255-4262; Thomson R, et al., In Principles of Tissue Engineering; Lanza R, Langer R and Vacanti J, eds. Academic Press: San Diego, pp. 251-262, 2000). The mitigation of nutrient transport limitations, external to three-dimensional cell/polymer constructs, influences the proliferation, differentiation, and expression of osteoblastic markers of MSCs seeded on three-dimensional scaffolds (Sikavitsas V I. Et al., J Biomed Mater Res 62: 136-148). The structural characterization showed that the pore size and the porosity of the water-silk sponge were controlled by the size of the NaCl particulates. We prepared the water-silk sponge with the regulated pore size (920±50 μm), which had more than 90% of the porosity. Furthermore, the pores were opened to the outside, interconnected and were uniformly distributed throughout the sponges.

Porous silk scaffolds were seeded with human BMSCs, and BMSCs-silk constructs were cultured for an extended period of 28 days in two model silk scaffolds (water-silk scaffolds and HFIP-silk scaffolds). The BMSCs seeded in water-silk scaffolds demonstrated accelerated proliferation during the first 2 weeks of culture, and the strongest ALP activity and the highest calcium deposition at the end of the culture period.

The onset of skeletogenesis, whether during fetal development or adult repair, begins with the condensation of mesenchymal stem cells. Shortly after the condensation stage, cells in the central region of the aggregation begin to adopt a cartilaginous phenotype (Ferguson C. et al., Mech. Dev. 1999, 87: 57-66). The expression of Col II showed this event in our silk scaffolds. Our investigation of Col II showed that despite the gene expression of Col II in early stage, differentiated BMSCs cultured in water-silk scaffolds maintained a differentiated phenotype to the end of the culture period. In early stage, we observed Col II expression expression in HFIP-silk constructs, too. But the Col II gene expression and protein expression were significantly reduced.

Chondrocytes progress from a proliferative to a hypertrophic state. The majority of hypertrophic chondrocytes are ultimately fated to undergo programmed cell death, which is accompanied by remodeling of the extracellular matrix (ECM) and the subsequent deposition of new bone (Gerber H. et al., Nat. Med. 1999, 5: 623-628). MMP13 regulates remodeling of the hypertrophic cartilage matrix. The expression of MMP 13 observed in water-silk constructs, but not in HFIP-silk constructs, indicating that the cells in water-silk scaffold were mature and hypertrophic chondrocytes.

The switch from a cartilage template to a bone during endochondral bone formation is not a mere switch of cell phenotypes. The cartilaginous ECM is then replaced by the bone ECM. Proteoglycan synthesis, the expression of ALP, and the expression of type I collagen, but very little type II collagen, were detected in water-silk constructs. Although the expression of ALP and type I collagen, the markers of osteoblastic differentiation, were significantly increased in water-silk constructs, the other protein of bone, BSP thought to comprise 8-12% of the total noncollagenous protein, was expressed similarly in water-silk scaffolds and HFIP-silk scaffolds. Coexpression of type I and type II collagen demonstrated in a study (Nakagawa T. et al., Oral Diseases 2003, 9: 255-263) showing that chondrocytes change their phenotype to produce the bone-like matrix and remain within the endochondral bone.

One of the osteoblast markers, OP, appears to be highly expressed at two stages of osteogenesis: at an early, proliferative stage and at a later stage, subsequent to the initial formation of mineralized bone matrix (Yae, K L. et al., J. Bone Miner. Res. 1994, 9: 231-240). Early in the culture, the expression of OP was upregurated in water-silk constructs. These studies point to the usefulness of water-silk scaffolds in the initial formation of bone tissue. Although type I collagen constitutes the largest portion (90%) of the organic matrix in bone, it is not unique to this tissue. Proteoglycan, or at least their component glycosaminoglaycan chains, have long been recognized as small but significant components of the mineralized bone matrix (Fisher L W. et al., J. Biol. Chem. 1982, 258: 6588-6594; Fedarko N S. Et al., J. Biol. Chem. 1990, 265: 12200-12209). After the culture in water-silk scaffolds, staining of sections with alcian blue stain clearly demonstrated the presence of proteoglycan in the ECM. Proteoglycan can be found in the cartilage. The origin and tissue specificity of these porteoglycans have not been determined. In our study, the proteoglycan was detected after 14 days of culture in water-silk constructs, but not in HFIP-silk constructs.

The references cited throughout the application are incorporated herein by reference.

What is claimed is:

1. A composition consisting essentially of at least 4% wt silk fibroin protein but not more than 10% wt silk fibroin protein, water, and a therapeutic agent.

2. The composition of claim 1, wherein said silk fibroin protein is obtained from a solution of dissolved silkworm silk, genetically engineered silk, or dissolved spider silk.

3. The composition of claim 1, wherein the therapeutic agent is a small molecule, a protein, a peptide, a polysaccharide, a glycoprotein, a lipoprotein, or a nucleic acid.

4. The composition of claim 1, wherein the therapeutic agent is a small molecule selected from the group consisting of vitamins, sedatives, hypnotics, antibiotics, antiviral agents, steroids, growth factor inhibitors, growth factor promoters, prostaglandins and radiopharmaceuticals.

5. The composition of claim 1, wherein the therapeutic agent is selected from the group consisting of anti-infectives, chemotherapeutic agents, anti-rejection agents, analgesics and analgesic combinations, anti-inflammatory agents, hormones, anti-angiogenic agents, anti-thrombotics, anti-metabolics, antimitotics, fibrinolytics, and growth factors.

6. The composition of claim 5, wherein the growth factor is selected from the group consisting of bone morphogenic proteins, bone morphogenic-like proteins, epidermal growth factor, fibroblast growth factor, platelet derived growth factor, insulin-like growth factor, transforming growth factors, and vascular endothelial growth factor.

7. The composition of claim 1, wherein the therapeutic agent is an antibody.

8. The composition of claim 1, wherein the therapeutic agent is present as a liquid or a finely divided solid.

9. The composition of claim 1, wherein the therapeutic agent further comprises a pharmaceutically acceptable carrier.

10. A composition consisting essentially of at least 4% wt silk fibroin protein but not more than 10% wt silk fibroin protein, water, and an additive.

11. The composition of claim 10, wherein said silk fibroin protein is obtained from a solution of dissolved silkworm silk, genetically engineered silk, or dissolved spider silk.

12. The composition of claim 10, wherein the additive is a biologically and/or pharmaceutically active compound.

13. The composition of claim 10, wherein the additive is an antibody, a deoxyribonucleic acid, a ribonucleic acid, a modified ribonucleic acid and protein composite, a glycogen, a sugar, an alcohol, or cytokine.

14. The composition of claim 10, wherein the additive is a cell attachment mediator, a biologically active ligand, a growth factor, or an osteoinductive substance.

15. The composition of claim 14, wherein the cell attachment mediator is selected from the group consisting of collagen, elastin, fibronectin, vitronectin, laminin, proteoglycans, a peptide containing known integrin binding domains and a combination thereof.

16. The composition of claim 14, wherein the growth factor is selected from the group consisting of fibroblast growth factor, epidermal growth factor, platelet-derived growth factor, insulin-like growth factor, transforming growth factor, and a combination thereof.

17. The composition of claim 14, wherein the osteoinductive substance is a bone morphogenic protein.

18. The composition of claim 10, wherein the additive is a bioactive substance that functions as a receptor or chemoattractant for a desired population of cells.

* * * * *